(12) United States Patent
Szabolcs

(10) Patent No.: US 9,114,100 B2
(45) Date of Patent: Aug. 25, 2015

(54) METHODS OF TREATMENT USING EX VIVO EXPANSION OF CORD BLOOD T CELLS

(75) Inventor: Paul Szabolcs, Fox Chapel, PA (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 13/698,604

(22) PCT Filed: May 17, 2011

(86) PCT No.: PCT/US2011/036795
§ 371 (c)(1),
(2), (4) Date: Nov. 16, 2012

(87) PCT Pub. No.: WO2011/146473
PCT Pub. Date: Nov. 24, 2011

(65) Prior Publication Data
US 2013/0058909 A1 Mar. 7, 2013

Related U.S. Application Data

(60) Provisional application No. 61/345,436, filed on May 17, 2010.

(51) Int. Cl.
*A61K 39/00* (2006.01)
*C12N 5/06* (2006.01)
*C12N 5/0783* (2010.01)

(52) U.S. Cl.
CPC .......... *A61K 39/0011* (2013.01); *C12N 5/0638* (2013.01); *A61K 2039/5158* (2013.01); *C12N 2501/2302* (2013.01); *C12N 2501/2307* (2013.01); *C12N 2501/2312* (2013.01); *C12N 2501/2315* (2013.01); *C12N 2501/51* (2013.01); *C12N 2501/515* (2013.01)

(58) Field of Classification Search
CPC .................. C12N 2501/2307; C07K 16/2818; C07K 16/2809; C07K 14/5418
See application file for complete search history.

(56) References Cited

U.S. PATENT DOCUMENTS

| | | | |
|---|---|---|---|
| 2002/0051784 A1 | 5/2002 | Boussiotis et al. | |
| 2004/0175827 A1* | 9/2004 | Fowler et al. | 435/372 |
| 2010/0035282 A1* | 2/2010 | Bonini et al. | 435/7.24 |
| 2013/0058909 A1 | 3/2013 | Szabolcs | |

OTHER PUBLICATIONS

Mercier-Letondal et al., Cytotherapy (2008) vol. 10, No. 3, 275-288.*
Morales et al., Cancer Immunol Immunother. 2009; 58(6): 941-953.*
Cha et al., Breast Cancer Res Treat (2010) 122:359-369.*
Cartellieri et al., PLoS ONE 9(4): e93745. doi:10.1371/journal.pone.0093745.*
Zeng et al., in press, Immunobiology 2014 http://dx.doi.org/10.1016/j.imbio.2014.03.003; 10 pages.*
Bere et al., Journal of Immunological Methods 354 (2010) 68-79.*
Liu et al., J Immunother 2006; 29:284-293.*
Robinson et al., Experimental Hematology 30 (2002) 245-251.*
Sanchez et al., Bone Marrow Transplantation (2003) 31, 713-723.*
Caserta et al. (Eur. J. Immunol. 2010. 40: 470-479).*
Wolfi et al. (Blood. 2007;110:201-210).*
Ho et al., (Journal of Immunological Methods 310 (2006) 40-52).*
Jeras et al. (Journal of Biomedicine and Biotechnology, 2010; vol. 2010, Article ID 705215, 15 pages).*
Kittipatarin et al. (J Immunol Methods. May 15, 2009; 344(1): 45-57).*
June C. (J. Clin. Invest. 117:1466-1476 (2007)).*
Nady et al. (Clinical and Vaccine Immunology, Jun. 2009, p. 798-805).*
Alpdogan O, Muriglan SJ, Eng JM, et al. "IL-7 enhances peripheral T cell reconstitution after allogeneic hematopoietic stem cell transplantation." J Clin Invest 2003; 112(7): 1095-107.
Alpdogan O, Schmaltz C, Muriglan SJ, et al. "Administration of interleukin-7 after allogeneic bone marrow transplantation improves immune reconstitution without aggravating graft-versus-host disease." Blood 2001;98(7):2256-65.
Aqui, N.A. et al., "Post-transplant adoptive T-cell immunotherapy," Best Pract. Res. Clin. Haematol. (2008) 21(3):503-519.
Azevedo RI, Soares MV, Barata JT, et al. "IL-7 sustains CD31 expression in human naive CD4+ T cells and preferentially expands the CD31 + subset in a PBK-dependent manner." Blood 2009; 113(13):2999-3007.
Azuma, M. et al. "B70 antigen is a second ligand for CTLA-4 and CD28" (1993) Nature 366:76-79.
Bird et al. "Single-Chain Antigen-Binding Proteins" (1988) Science 242:423-426.
Bolotin E, Arnett G, Parkman R, Weinberg K. "Serum levels of IL-7 in bone marrow transplant recipients: relationship to clinical characteristics and lymphocyte count." Bone Marrow Transplant 1999;23(8):783-8.
Broxmeyer HE, American Association of Blood Banks. "Cord blood biology, immunology, and clinical transplantation." Bethesda, Md.: AABB Press; 2004.
Chalmers IM, Janossy G, Contreras M, Navarrete C. "Intracellular cytokine profile of cord and adult blood lymphocytes." Blood 1998;92(1): 11-8.
Chen, H-W. et al., "Ex vivo expansion of dendritic-cell-activated antigen-specific CD4 T cells with anti-CD3/CD28, interleukin-7, and interleukin-15: potential for adoptive T cell immunotherapy," Clin. Immunol (2006) 119:21-31.
Chung B, Dudl E, Toyama A, Barsky L, Weinberg K I. "Importance of interleukin-7 in the development of experimental graft-versus-host disease." Biol Blood Marrow Transplant 2008; 14(1): 16-27.
Chung B, Dudl EP, Min D, Barsky L, Smiley N, Weinberg KI. "Prevention of graftversus-host disease by anti IL-7Ralpha antibody." Blood 2007;110(8):2803-10.
Dardalhon V, Jaleco S, Kinet S, et al. "IL-7 differentially regulates cell cycle progression and HIV-1-based vector infection in neonatal and adult CD4+ T cells." Proc Natl Acad Sci USA 2001;98(16):9277-82.

(Continued)

*Primary Examiner* — Ilia Ouspenski
(74) *Attorney, Agent, or Firm* — Michael Best & Friedrich LLP

(57) ABSTRACT

Provided are methods of enhancing ex vivo proliferation of a T cell population, the methods comprising contacting the T cell population with IL-7 and anti-CD3/CD28 antibody to activate and expand the T cell population. Further provided are methods of generating an antigen-specific cytotoxic T cell population comprising priming a CD3/CD28-expanded T cell population against an antigen (e.g., a cancer cell) in the presence of at least one of IL-7, IL-12, and IL-15, or a combination thereof. Further provided are methods of treating T cell lymphopenia in a subject, comprising administering a CD3/CD28-expanded T cell population to the subject.

7 Claims, 10 Drawing Sheets

(56) References Cited

OTHER PUBLICATIONS

Dardalhon V, Jaleco S, Rebouissou C, et al. "Highly efficient gene transfer in naïve human T cells with a murine leukemia virus-based vector." Blood 2000;96(3):885-93.

Freedman, A. S. et al. "B7, A B Cell-Restricted Antigen That Identifies Preactivated B Cells." (1987) J. Immunol. 137:3260-3267.

Freeman, G. J. et al. "B7, A New Member of the Ig Superfamily with Unique Expression on Activated and Neoplastic B Cells." (1989) J. Immunol. 143:2714-2722.

Freeman, G. J. et al. "Structure, Expression, and T Cell Costimulatory Activity of the Murine Homologue of the Human B Lymphocyte Activation Antigen B7." (1991) J. Exp. Med. 174:625-631.

Freeman, G. J. et al. "Murine B7-2, an Alternative CTLA4 Counter-receptor that Costimulates T Cell Proliferation and Interleukin 2 Production." (1993) J. Exp. Med. 178:2185-2192.

Freeman, G. J. et al. "Cloning of B7-2: A CTLA-4 Counter-Receptor that Costimulates Human T Cell Proliferation." (1993) Science 262:909-911.

Fujita Y, Rooney CM, Heslop HE. "Adoptive cellular immunotherapy for viral diseases." Bone Marrow Transplant 2008, 41, 193-8.

Fukui T, Katamura K, Abe N, et al. "IL-7 induces proliferation, variable cytokineproducing ability and IL-2 responsiveness in naive CD4+ T-cells from human cord blood." Immunol Lett 1997;59(1):21-8.

Goodwin VJ, Sato TA, Mitchell MD, Keelan JA. "Anti-inflammatory effects of interleukin-4, interleukin-10, and transforming growth factor-beta on human placental cells in vitro." Am J Reprod Immunol 1998, 40, 319-25.

Hagihara M, Chargui J, Gansuvd B, et al. "Umbilical cord blood T lymphocytes are induced to apoptosis after being allo-primed in vitro." Bone Marrow Transplant 1999;24(11 ): 1229-33.

Harris DT, LoCascio J, Besencon Fl. "Analysis of the alloreactive capacity of human umbilical cord blood: implications for graft-versus-host disease." Bone Marrow Transplant 1994, 14, 545-553.

Hexner EO, Danet-Desnoyers GA, Zhang Y, et al. "Umbilical cord blood xenografts in immunodeficient mice reveal that T cells enhance hematopoietic engraftment beyond overcoming immune barriers by stimulating stem cell differentiation." Biol Blood Marrow Transplant 2007; 13(10): 1135-44.

Huston et al. "Protein engineering of antibody binding sites: Recovery of specific activity in an anti-digoxin single-chain Fv analogue produced in *Escherichia coli*." (1988) PNAS 85:5879-5883.

Jaleco S, Swainson L, Dardalhon V, Burjanadze M, Kinet S, Taylor N. "Homeostasis of naive and memory CD4+ T cells: IL-2 and IL-7 differentially regulate the balance between proliferation and Fas-mediated apoptosis." J Immunol 2003; 171(1):61-8.

June CH, Ledbetter JA, Linsley PS, Thompson CB. "Role of the CD28 receptor in T-cell activation." Immunol Today 1990;11(6):211-6.

Kepler TB, He M, Tomfohr JK, Devlin BH, Sarzotti M, Markert ML. "Statistical analysis of antigen receptor spectratype data." Bioinformatics 2005, 21, 3394-400.

Klein AK, Patel DD, Gooding ME, et al. "T-Cell recovery in adults and children following umbilical cord blood transplantation." Biol Blood Marrow Transplant 2001, 7, 454-66.

Komanduri KV, StJohn LS, de Lima M, et al. "Delayed immune reconstitution after cord blood transplantation is characterized by impaired thymopoiesis and late memory T-cell skewing." Blood 2007; 110(13):4543-51.

Laport GG, Levine BL, Stadtmauer EA, et al. "Adoptive transfer of costimulated T cells induces lymphocytosis in patients with relapsed/refractory non-Hodgkin lymphoma following CD34+-selected hematopoietic cell transplantation." Blood 2003;102(6):2004-13.

Levine BL, Bernstein WB, Aronson NE, et al. "Adoptive transfer of costimulated CD4+ T cells induces expansion of peripheral T cells and decreased CCR5 expression in HIV infection." Nat Med 2002;8(1):47-53.

Lu H, Zhao Z, Kalina T, et al. "Interleukin-7 improves reconstitution of antiviral CD4 T cells." Clin Immunol 2005; 114(1):30-41.

Mackall CL, Fry TJ, Bare C, Morgan P, Galbraith A, Gress RE. "IL-7 increases both thymic-dependent and thymic-independent T-cell regeneration after bone marrow transplantation." Blood 2001;97(5): 1491-7.

Managlia EZ, Landay A, Al-Harthi L. "Interleukin-7 signalling is sufficient to phenotypically and functionally pnme human CD4 naive T cells." Immunology 2005; 114(3):322-35.

Marchant A, Goldman M. "T cell-mediated immune responses in human newborns: ready to learn?" Clin Exp Immunol 2005, 141, 10-8.

Mazur MA, Davis CC, Szabolcs P. "Ex vivo expansion and Thi/Tcl maturation of umbilical cord blood T cells by CD3/CD28 costimulation." Bioi Blood Marrow Transplant 2008, 14, 1190-6.

Moniuszko M, Fry T, Tsai WP, et al. "Recombinant interleukin-7 induces proliferation of naive macaque CD4+ and CD8+ T cells in vivo." J virol 2004;78(18):9740-9.

Park KD, et al., "In vitro priming and expansion of cytomegalovirus-specific Th1 and Tc1 T cells from naïve cord blood lymphocytes." Blood, (2006);108:1770-3.

Parkman R, Cohen G, Carter SL, et al. "Successful immune reconstitution decreases leukemic relapse and improves survival in recipients of unrelated cord blood transplantation." Biol Blood Marrow Transplant 2006;12(9):919-27.

Parmar S, Robinson SN, Komanduri K, et al. "Ex vivo expanded umbilical cord blood T cells maintain naive phenotype and TCR diversity." Cytotherapy 2006;8(2): 149-57.

Porter DL, Levine BL, Bunin N, et al. "A phase 1 trial of donor lymphocyte infusions expanded and activated ex vivo via CD3/CD28 costimulation." Blood 2006; 107(4): 1325-31.

Reddy P, Arora M, Guimond M, Mackall CL. "GVHD: a continuing barrier to the safety of allogeneic transplantation." Biol Blood Marrow Rev 2009; 15(1 Suppl): 162-8.

Rosenberg SA, Sportes C, Ahmadzadeh M, et al. "IL-7 administration to humans leads to expansion of CD8+ and CD4+ cells but a relative decrease of CD4+ T-regulatory cells." J Immunother 2006;29(3):313-9.

Schluns KS, Kieper WC, Jameson SC, Lefrancois L. "Interleukin-7 mediates the homeostasis of naive and memory CD8 T cells in vivo." Nat Immunol 2000;1(5):426-432.

Schluns, K.S. et al., "Cutting edge: requirement for IL-15 in the generation of primary and memory antigen-specific CD8 T cells," J. Immunol. (2002) 168:4827-4831.

Sinha ML, Fry TJ, Fowler DH, Miller G, Mackall CL. "Interleukin 7 worsens graftversus-host disease." Blood 2002; 100(7):2642-9.

Snyder KM, Mackall CL, Fry TJ. "IL-7 in allogeneic transplant: clinical promise and potential pitfalls." Leuk Lymphoma 2006;47(7): 1222-8.

Soares MV, Borthwick NJ, Maini MK, Janossy G, Salmon M, Akbar AN. "IL-7-dependent extrathymic expansion of CD45RA+ T cells enables preservation of a naïve repertoire." J Immunol 1998; 161(11):5909-17.

Sportes C, Hakim FT, Memon SA, et al. "Administration of rhiL-7 in humans increases in vivo TCR repertoire diversity by preferential expansion of naive T cell subsets." J Exp Med 2008; 205(7): 1701-14.

Stonehouse T J, Woodhead VE, Herridge PS, et al. "Molecular characterization of U937-dependent T-cell costimulation." Immunology 1999, 96, 35-47.

Surh CD, Boyman O, Purton JF, Sprent J. "Homeostasis of memory T cells." Immunol Rev 2006;211: 154-63.

Szabolcs P, Niedzwiecki D. "Immune reconstitution after unrelated cord blood transplantation." Cytotherapy 2007;9(2): 111-22.

Szabolcs P, Park KD, Marti L, et al. "Superior depletion of alloreactive T cells from peripheral blood stem cell and umbilical cord blood grafts by the combined use of trimetrexate and interleukin-2 immunotoxin." Bioi Blood Marrow Transplant 2004, 10, 772-83.

Szabolcs P, Park KD, Reese M, Marti L, Broadwater G, Kurtzberg J. "Absolute values of dendritic cell subsets in bone marrow, cord blood, and peripheral blood enumerated by a novel method." Stem Cells 2003;21(3):296-303.

(56) References Cited

OTHER PUBLICATIONS

Szabolcs P, Park KD, Reese M, Marti L, Broadwater G, Kurtzberg J. "Coexistent naive phenotype and higher cycling rate of cord blood T cells as compared to adult peripheral blood." Exp Hematol 2003, 31, 708-14.

Tan JT, Dudl E, LeRoy E, et al. "IL-7 is critical for homeostatic proliferation and survival of naive T cells." Proc Natl Acad Sci USA 2001;98(15):8732-7.

Vakkila J, Aysto S, Saarinen-Pihkala UM, Sariola H. "Naive CD4+ T cells can be sensitized with IL-7." Scand J Immunol 2001;54(5): 501-5.

van den Brink MR, Alpdogan O, Boyd RL. "Strategies to enhance T-cell reconstitution in immunocompromised patients." Nature reviews 2004;4(11):856-67.

Ward et al., "Binding activites of a repertoire of single immunoglobulin variable domains secreted from *Escherichia coli*." (1989) Nature 341:544-546.

Webb LM, Foxwell BM, Feldmann M. "Interleukin-7 activates human naive CD4+ cells and primes for interleukin-4 production." Eur J Immunol 1997;27(3):633-40.

International Search Report and Written Opinion for Application No. PCT/US2011/36795 dated Aug. 15, 2011 (8 pages).

* cited by examiner

A

B

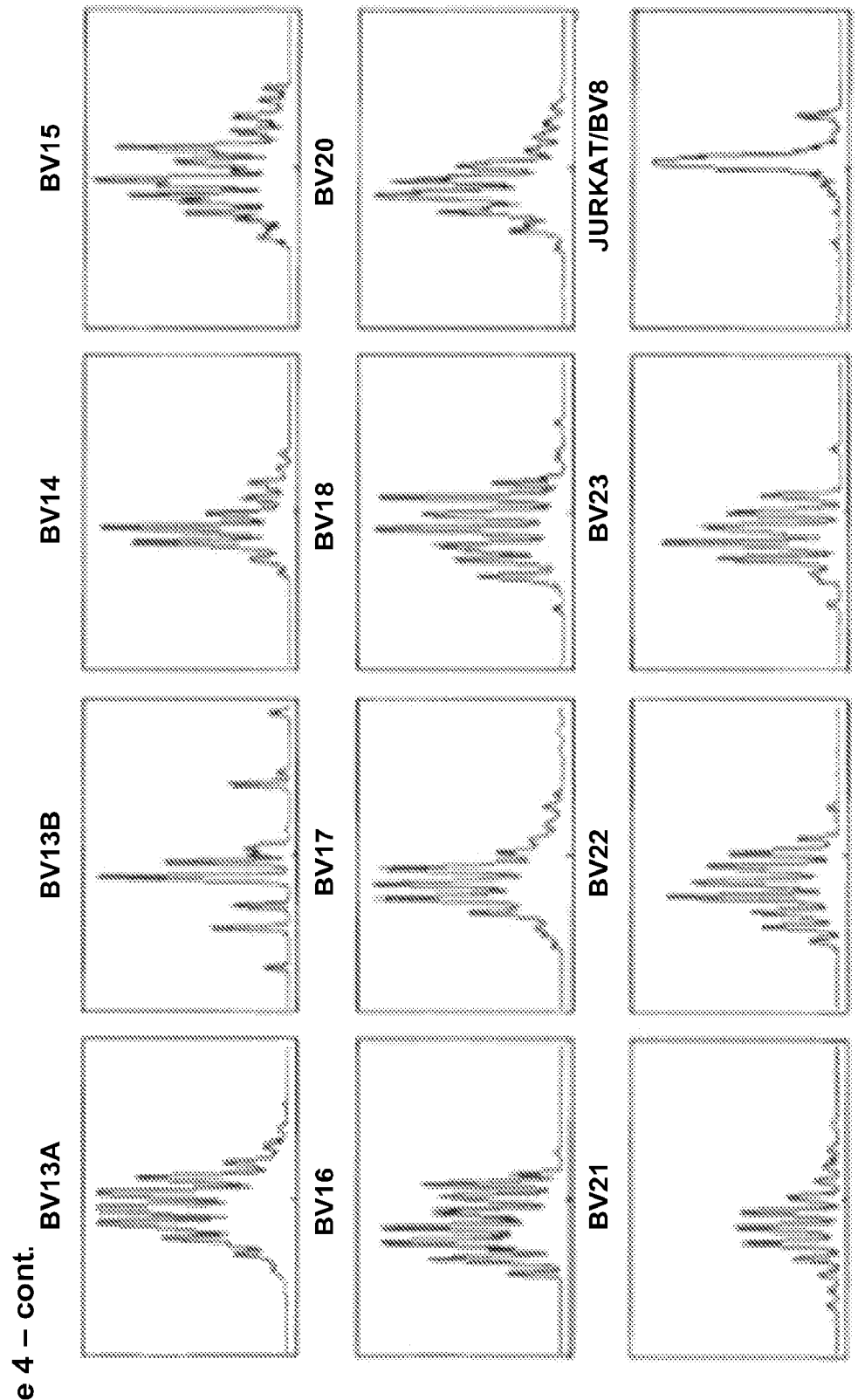
Figure 4 – cont.

A.

B.

METHODS OF TREATMENT USING EX VIVO EXPANSION OF CORD BLOOD T CELLS

CROSS-REFERENCE TO RELATED APPLICATIONS

This application is a national stage filing un 35 U.S.C. 371 of International Patent Application No. PCT/US2011/036795, filed May 17, 2011, which claims the benefit of priority to U.S. Provisional Patent Application No. 61/345,436, filed May 17, 2010, which are incorporated herein by reference in their entireties. Priority to each application is hereby claimed.

STATEMENT REGARDING FEDERALLY SPONSORED RESEARCH

This invention was made with government support under grants R01-CA132110, Al58607, and Al51445 awarded by the National Institutes of Health. The government has certain rights in the invention.

BACKGROUND

The development of techniques for propagating T cell populations in vitro has been crucial to many of the recent advances in the understanding of T cell recognition of antigen and T cell activation. The development of culture methods for the generation of human antigen-specific T cell clones has been useful in defining antigens expressed by pathogens and tumors that are recognized by T cells to establish methods of immunotherapy to treat a variety of human diseases. Antigen-specific T cells can be expanded in vitro for use in adoptive cellular immunotherapy in which infusions of such T cells have been shown to have anti-tumor reactivity in a tumor-bearing host. Adoptive immunotherapy has also been used to treat viral infections in immunocompromised individuals.

Donor leukocyte infusions (DLI) in the allogeneic hematopoietic transplant setting can provide a clinically relevant boost of immunity to reduce opportunistic infections and to increase graft-versus-leukemia activity. Despite significant advances in applicability, DLI has not been available for single-unit recipients of unrelated cord blood transplant. Ex vivo expansion of cord blood T cells can be achieved with interleukin 2 (IL-2) and CD3/CD28 co-stimulatory beads. However, significant apoptosis occurs in proliferating T cells, diminishing the yield and skewing the CD4/CD8 ratio in the T-cell population, jeopardizing the potential efficacy of DLI.

Lymphopenia is one consequence of hematopoietic cell transplantation. DLI may be used to treat lymphopenia by transferring naturally primed and typically resting, unmanipulated leukocytes. T lymphocytes represent a fraction of the total leukocytes present in blood, ranging typically between 20-30%. To correct T cell lymphopenia, however, more cells are needed than is available. Once cord blood grafts are thawed and the majority infused, there is insufficient numbers available. Besides the numerical shortage, T lymphocytes present in cord blood are also antigen inexperienced and functionally impaired/hyporesponsive, rendering them less suitable for treating infections.

Accordingly, alternative methods for expanding T cell populations, such as from cord blood, which lack alloreactivity against a host or host's cells, and methods for generating antigen-specific cytotoxic T cells from expanded T cell populations would be beneficial.

SUMMARY

In an aspect the disclosure relates to a method of enhancing ex vivo proliferation of a T cell population comprising contacting the T cell population with IL-7, an anti-CD3 antibody, and an anti-CD28 antibody, or functional fragments thereof, to activate and expand the T cell population.

In an aspect the disclosure relates to a method for generating an antigen-specific cytotoxic T cell population comprising priming a T cell population that has been expanded according to the methods herein described against an antigen in the presence of at least one of IL-15, IL-12, or IL-7, or a combination thereof.

In an aspect the disclosure relates to a method for generating a tumor-specific cytotoxic T cell population comprising priming a T cell population that has been expanded according to the methods herein described against a cancer cell in the presence of at least one of IL-15, IL-12, or IL-7, or a combination thereof.

In an aspect the disclosure provides a method for treating T cell lymphopenia in a subject in need of treatment, comprising administering to the subject an amount of a T cell population that is expanded according to the methods disclosed herein.

In an aspect the disclosure relates to a donor leukocyte infusion product comprising a T cell population that is expanded according to the methods disclosed herein.

In an aspect the disclosure relates to a method for reducing proliferation of a cancer cell comprising expanding a T cell population by contacting the T cell population with IL-7, an anti-CD3 antibody, and an anti-CD28 antibody, or functional fragments thereof, with IL-7, IL-2, and anti-CD3/CD28 antibodies to activate and expand the T cell population; priming at least one T cell in the expanded T cell population against a cancer cell in the presence of at least one of IL-15, IL-7, or IL-12, or a combination thereof to generate at least one tumor-specific cytotoxic T cell, and contacting the cancer cell with the at least one tumor-specific cytotoxic T cell.

The disclosure provides for other aspects and embodiments that will be apparent in light of the following detailed description.

DETAILED DESCRIPTION

Figure 1:
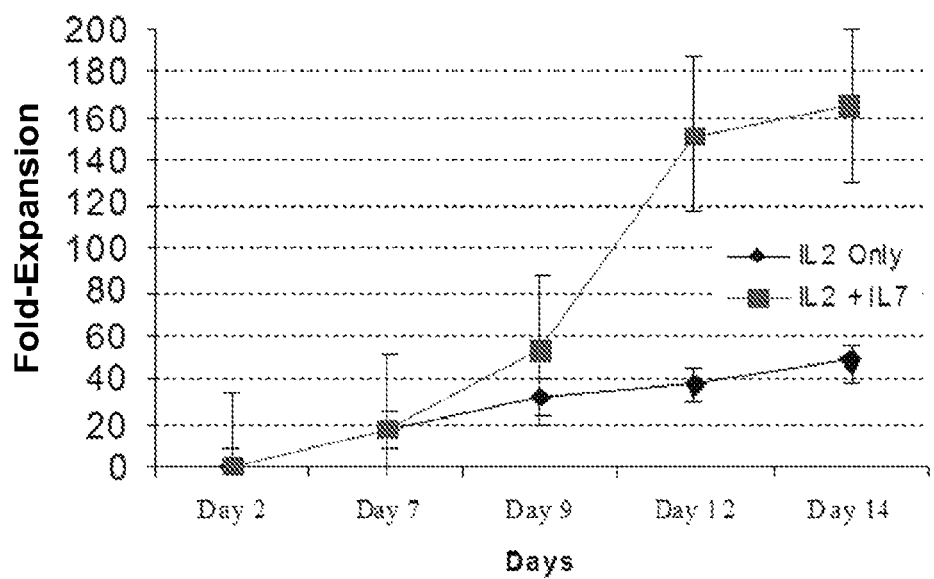
FIG. 1A is a graph showing increased expansion of T cells in the presence of IL-2 and IL-7 compared to only IL-2.
FIG. 1B is a graph showing loss of sjTREC for both T cells expanded in the presence of IL-2 and IL-7 as well as only IL-2.
Figure 1:
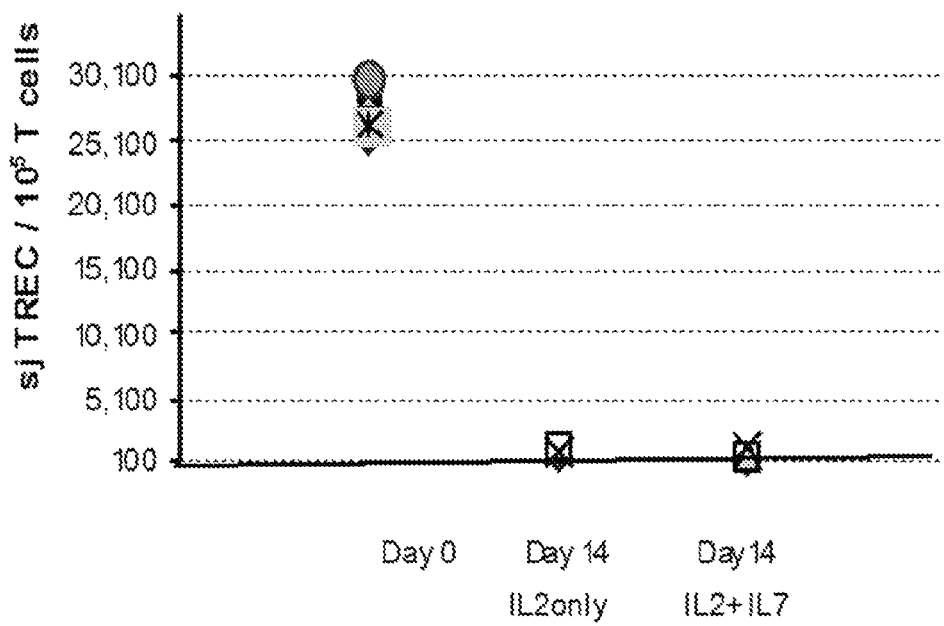

In a general sense the disclosure provides a relatively simple, reproducible method for ex vivo expansion of T cells that meet both numerical and qualitative biological benchmarks for use of such T cells as DLI in the clinic (e.g., donor cord blood transplantation (DCBT) setting). Donor leukocyte infusions with ex vivo expanded T cells from the originally infused graft can be used to alleviate conditions such as post-transplant lymphopenia and qualitative T cell defects well before thymic regeneration can contribute new T cells. For example, by starting with ~$2 \times 10^6$ total CB T cells, easily obtainable by using 2-3% of a typical UCB graft, ~100 fold expansion would yield ~$2 \times 10^6$ cells/kg for patients up to 90 kg. It is anticipated that dose escalation/phase I trials will be started at lower doses in HLA-mismatched UCBT setting to test safety while testing for augmented cellular immune function in a prophylactic manner for high risk patients such as those with viral reactivation and severe lymphopenia. As certain embodiments of the methods provide an antigen non-specific expansion strategy, the methods and resulting expanded T cell populations provide for further methods that generate and expand large numbers of antigen-specific (e.g., tumor-specific) CTL available for adoptive transfer to treat various diseases and disorders (e.g., residual and/or relapsed leukemia post-transplantation).

In an aspect, the disclosure provides methods for inducing ex vivo expansion of a population of T cells. T cell proliferation can be induced without the need for antigen, thus providing an expanded T cell population which is polyclonal with respect to antigen reactivity. Embodiments of the method provide for sustained proliferation of a population of T cells over an extended period of time to yield a multi-fold increase in the number of cells relative to the original T cell population. This aspect can comprise a method of enhancing ex vivo proliferation of a T cell population comprising contacting the T cell population with IL-7, an anti-CD3 antibody, and an anti-CD28 antibody, or functional fragments thereof, to activate and expand the T cell population. In some embodiments, the T cell population may be further contacted with IL-2. Suitably an increased population of CD3/CD28-expanded T cells is generated by the method. In certain embodiments, methods are provided for generating a population of CD3/CD28-expanded T cells, the methods comprising contacting the T cell population with IL-7 and anti-CD3/CD28 antibodies to activate and expand the T cell population. Embodiments provide for a T cell population that is taken or isolated from cord blood. In some embodiments the method provides for the generation of activated and expanded T cells in about 10 to about 20 days, and in some embodiments about 14 days.

As used herein, a "CD3/CD28-expanded T cell" refers to a T cell that has been co-stimulated by contact with anti-CD3 and anti-CD28 antibodies. As used herein anti-CD3, anti-CD28, and anti-CD3/CD28 antibodies refer to any molecule or complex that interacts with both CD3 and CD28 receptors on the T cell. While it is shown below in the Examples that T cells may be contacted with beads with anti-CD3/CD28 antibodies, it is envisioned that the antibodies may be presented on surfaces including but not limited to particles, beads, and cells. Hence, T cells may be contacted with any molecule or complex that interacts with both CD3 and CD28 receptors on the T cell, wherein the complexes may be presented on surfaces including but not limited to particles, beads, and cells.

In some embodiments, a population of T cells is induced to proliferate (or "expand," "propagate," "grow," and the like) by contacting the T cells with IL-7 in combination with a molecule that can active the T cells and with a molecule that can stimulate the T cells under conditions suitable for inducing expansion of at least one T cell, or a portion, a plurality, a majority, or substantially all T cells that contact the molecule that can activate and the molecule that can stimulate the T cell(s). The contacting of the T cell can be accomplished by any suitable method known in the art, either sequentially or simultaneously. In embodiments that comprise sequential contacting strategies, the T cell is suitably first contacted with an agent that can activate the T cell and subsequently contacted with an agent that can stimulate the T cell and induce proliferation.

In some embodiments, activation of a population of T cells is accomplished by contacting the T cells with a first agent which induces or activates a TCR/CD3 complex-associated signal in the T cells. In embodiments the activation of the TCR/CD3 complex-associated signal in a T cell can be accomplished either by ligation of the T cell receptor (TCR)/CD3 complex, or by directly stimulating receptor-coupled signaling pathways. In embodiments, an anti-CD3 antibody can be used to activate a population of T cells.

In some embodiments proliferation of an activated T cell population can be induced to proliferate by contacting the activated T cells with a second agent which stimulates an accessory molecule on the surface of the T cells. In embodiments a population of CD4$^+$ T cells can be stimulated to proliferate with an anti-CD28 antibody directed to the CD28 molecule on the surface of the T cells. Embodiments also provide for stimulation by other natural ligands for CD28, which can be soluble, on a cell membrane, or coupled to a solid phase surface. In some embodiments, proliferation of an activated population of T cells can be induced by stimulation of one or more intracellular signals which result from ligation of an accessory molecule.

In some embodiments, the agent provides the primary activation signal and the agent providing the co-stimulatory agent can be added either in soluble form or coupled to a solid phase surface. In some embodiments, the two agents are coupled to the same solid phase surface such as, for example, the surface of a cell culture vessel or a particle (e.g., microparticle, nanoparticle, beads including magnetic beads, polymeric beads, glass beads, and the like). In embodiments the methods can comprise contacting a costimulatory signal to a T cell for T cell expansion (e.g., an anti-CD28 antibody or an active fragment thereof), coupled to a solid phase surface which may additionally include an agent that provides a primary activation signal to the T cell (e.g., an anti-CD3 antibody or an active fragment thereof) coupled to the same solid phase surface. In some embodiments the agents are attached to beads. Compositions comprising each agent coupled to different solid phase surfaces (i.e., an agent that provides a primary T cell activation signal coupled to a first solid phase surface and an agent that provides a costimulatory signal coupled to a second solid phase surface) are also within the scope of the disclosure.

Following activation and stimulation of the T cells, the proliferation of the T cells in response to continuing exposure to the agents can be monitored by any suitable method known in the art. When the rate of T cell proliferation decreases, the T cells can be reactivated and restimulated, such as with additional anti-CD3 antibody and anti-CD28 antibody, or active fragments thereof, to induce further proliferation. In an embodiment, the rate of T cell proliferation is monitored by examining cell size. Alternatively, an embodiment provides for monitoring T cell proliferation by assaying for expression of cell surface molecules in response to exposure to the molecules, such as anti-CD3/CD28 antibodies. The monitoring and restimulation of the T cells can be repeated for sustained proliferation to produce a population of T cells increased in number from about 100- to about 100,000-fold or more relative to the original T cell population. As noted above, some embodiments provide for methods that expand the T cell population in about 7 days, about 10 days, about 14 days, or about 20 days.

The method of the invention can be used to expand selected T cell populations for use in treating a disease or disorder such as, for example lymphopenia or cancer. In embodiments that relate to the treatment of a disease, the method suitably comprises priming one or a plurality of the expanded T cell population with an antigen of interest such as, for example, a cancer cell, under conditions that produce an antigen-specific T cell population. The resulting T cell population can be used for therapy or can be used for in vitro analysis of the disease, such as cancer. In embodiments, a population of tumor-infiltrating lymphocytes can be obtained from a subject afflicted with cancer and the T cells stimulated to proliferate to sufficient numbers and restored to the subject.

The term "T cell activation" is used herein to define a state in which a T cell response has been initiated or activated by a primary signal, such as through the TCR/CD3 complex, but not necessarily due to interaction with a protein antigen. A T cell is activated if it has received a primary signaling event which initiates an immune response by the T cell. In embodiments, T cell activation can be accomplished by stimulating the T cell TCR/CD3 complex. An anti-CD3 monoclonal antibody can be used to activate a population of T cells via the TCR/CD3 complex. A number of anti-human CD3 monoclonal antibodies are commercially available. Other antibodies which bind to the same epitopes as an anti-CD3 antibody can also be used. Additional antibodies, or combinations of antibodies, can be prepared and identified by techniques known in the art.

The activated population of T cells can be induced to proliferate (i.e., a population of T cells that has received a primary activation signal induced by an anti-CD3 antibody) by stimulation of the accessory molecule CD28 by contacting an activated population of T cells with a ligand which binds CD28. In embodiments, an anti-CD28 monoclonal antibody or fragment thereof capable of crosslinking the CD28 molecule, or a natural ligand for CD28 (e.g., a member of the B7 family of proteins, such as B7-1(CD80) and B7-2 (CD86) (Freedman, A. S. et al. (1987) J. Immunol. 137:3260-3267; Freeman, G. J. et al. (1989) J. Immunol. 143:2714-2722; Freeman, G. J. et al. (1991) J. Exp. Med. 174:625-63 1; Freeman, G. J. et al. (1993) Science 262:909-911; Azuma, M. et al. (1993) Nature 366:76-79; Freeman, G. J. et al. (1993) J. Exp. Med. 178:2185-2192)) can be used to induce stimulation of the CD28 molecule. In embodiments the molecule comprises an anti-CD28 antibody or an active fragment thereof. A number of anti-CD28 antibodies are known in the art and are commercially available.

For T cell costimulation, IL-7 and the agents that activate and induce expansion can be provided to the T-cells, and incubated with the T cells to be co-stimulated. The ratio of T cells to stimulating agents can vary widely, depending on the source of the agent(s). In embodiments comprising use of soluble agents (e.g., anti-CD3/CD28 antibodies), soluble agents are added to the T cell culture in an amount sufficient to result in co-stimulation of activated T cells, in combination with IL-7. The appropriate amount of soluble agent to be added will vary with the specific agent, but can be determined by assaying different amounts of the soluble agent in T cell cultures and measuring the extent of co-stimulation by proliferation assays or production of cytokines. Typically in embodiments comprising anti-CD3 and anti-CD28 antibodies, such agents can be provided at concentrations typically ranging from 0.01 ng to about 100 mg/nL, or to about 100 ng/mL, or in some embodiments from about 10 ng to about0 50 mg/mL. In embodiments comprising one or more agents attached to a substrate such as, for example ClinExVivo Dynabeads (Dynal/Invitrogen Corp.), an excess number of beads per cell in culture can be provided, such as about 2:1, 3:1, 4:1, 5:1, 6:1, 7:1, 8:1, 9:1, 10:1, 15:1, 20:1, 25:1, or even 50:1, or more beads:T cell (as measured in the initial culture). In some embodiments, the amount of the activation and/or stimulatory agents can be determined and/or adjusted based on the response of the culture after contacting, as measured by the T cell response. Similarly the amount of IL-7 contacted with the T cell population can vary from about 0.01 ng to about 100 mg/mL, or in some embodiments from about 1.0 ng to about 100 ng/mL, or about 1.0 ng to about 10.0 ng/mL.

In another embodiment, a natural ligand of CD28 (B7-1, B7-2) can be presented to T cells in a form attached to a solid phase surface, such as beads. These molecules can then be attached to the solid phase surface via conventional techniques (e.g., covalent modification using tosyl linkage to tosyl activated magnetic immunobeads (Dynal Inc., Great Neck, N.Y.) according to manufacturer's instructions.) The molecules may also be immobilized on modified polystyrene beads or culture vessel surfaces (e.g., through an avidin- or streptavidin-biotin complex). In such embodiments, the soluble molecule(s) can be crosslinked to biotin and then reacted with the solid phase surface to which avidin or streptavidin molecules are bound. Conversely, the soluble molecules can be crosslinked to avidin or streptavidin and reacted with a solid phase surface that is derivatized with biotin molecules.

Standard techniques such as, for example FACS analysis can be used to determine the amount of molecules bound to a solid phase surface such as particles, beads, etc. or by ELISA if the solid phase surface is that of a tissue culture dish. Antibodies reactive with the antibody molecules (e.g., anti-CD3/CD28 antibodies) can be used in these assays.

In another aspect, the disclosure provides a method for generating or expanding a population of antigen specific T cells. In some embodiments, the method comprises priming an expanded T cell (such as by the methods described herein) against an antigen in the presence of at least one of IL-15, IL-12, or IL-7, or a combination thereof.

The antigen can be presented to the T cell by an antigen presenting cell in connection with an MHC molecule. An antigen presenting cell, such as a B cell, macrophage, monocyte, dendritic cell, Langerhan cell, or other cell which can present antigen to a T cell. Alternatively, a cell expressing an antigen of interest can be incubated with the T cell. For example, a tumor cell expressing tumor-associated antigens can be incubated with a T cell (e.g., from a T cell population expanded by the methods described herein) together with an amount of at least one of IL-15, IL-12, or IL-7, or a combination thereof, as to induce a tumor-specific response. In some embodiments, the method comprises priming a T cell population that is expanded according to the methods described herein, with an amount of IL-15. In some embodiments, the method comprises priming a T cell population with an amount of IL-15, IL-12, and IL-7. The primed T cell population can be contacted with the antigen of interest such as, for example, an antigen associated with a cancer cell, a cell infected with a pathogen, e.g., a virus, and the like that present antigens to the T cell. In some embodiments, following antigen specific activation of a population of T cells, the cells can be expanded in accordance with the methods described herein. For example, after antigen specificity has been established, T cells can be expanded by culture with an anti-CD3 antibody and an anti-CD28 antibody and IL-7 according to the methods described herein.

In some embodiments, the tumor-specific cytotoxic T cell may be administered to a subject, and the cancer cell may be from the same subject. In some embodiments, the cancer cells may be contacted with $IFN_\gamma$ to increase the immunogenicity. In some embodiments, the cancer cells may be attenuated or killed, for example, with radiation or chemotherapeutic agents (such as Mitomycin).

The term "antibody" as used herein refers to immunoglobulin molecules and immunologically active portions of immunoglobulin molecules, i.e., molecules that contain an antigen binding site which specifically binds (immunoreacts with) an antigen, such as CD3, CD28. It has been shown that the antigen-binding function of an antibody can be performed by fragments of a naturally-occurring antibody. Thus, these antigen-binding fragments are also intended to be designated by the term "antibody". Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., (1989) Nature 341:544-546) which consists of a VH domain; (v) an isolated complimentarity determining region (CDR); and (vi) an $F(ab')_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. (1988) Science 242:423-426; and Huston et al. (1988) PNAS 85:5879-5883) by recombinant methods. Such single chain antibodies are also encompassed within the term "antibody." Antibodies can be fragmented using conventional techniques as described herein and the fragments screened for utility in the same manner as described for whole antibodies.

As noted above, soluble forms of antibodies may be used to activate T cells, as well as antibodies immobilized on a solid phase surface (e.g., beads). An antibody can be immobilized directly or indirectly by, for example, by a secondary antibody, to a solid surface, such as a tissue culture flask or bead.

In certain embodiments, methods are provided for treating lymphopenia. The methods may comprise administering a CD3/CD28-expanded T cell, as described above, to a subject in need thereof. Lymphopenia can arise from or be associated with an infection, such as common cold or flu; corticosteroid use; infections with HIV and other viral, bacterial, and fungal agents; malnutrition; systemic lupus erythematosus; severe stress; intense or prolonged physical exercise (due to cortisol release); rheumatoid arthritis; sarcoidosis; iatrogenic conditions; chemotherapy (such as with cytotoxic agents or immunosuppressive drugs); malignancies such as leukemia or advanced Hodgkin's disease; radiation (large dose (e.g., accidental exposure or whole body radiation)); or post-transplant. In embodiments, the lymphopenia may be post-transplant lymphopenia, and the CD3/CD28-expanded T cell may be administered in a donor leukocyte infusion product.

Lymphocytopenia can be diagnosed by any suitable method, typically from the results of a complete blood count. In adults, a lymphocyte level below 1,500 cells/microliter is diagnostic (proof of the condition), and in children, a lymphocyte level below 3,000 cells/microliter is diagnostic.

In an aspect, the disclosure provides a donor lymphocyte infusion product comprising an expanded T cell population generated by the methods described herein. Donor lymphocyte (or leukocyte) infusion (DLI) or buffy coat fusion is a form of adoptive immunotherapy typically used after hematopoietic stem cell transplantation. Typically, donor leukocyte infusion comprises the administration of T cells modified (e.g., antigen-specific T cells) and/or expanded by the methods described herein, that optionally can be taken from the original cell donor to have the infusion, after the transplant, to augment an anti-tumor immune response or ensure that the donor stem cells remain engrafted. The methods provided herein allow for non-specific source of T cell population, such as for example cord blood stocks. These donated white blood cells contain cells of the immune system that can recognize and destroy cancer cells. DLI therapy can be designed to induce a remission of the subject's cancer by a process called the graft-versus-tumor effect (GVT). The donor T-cells can attack and control the growth of residual cancer cells providing the GVT effect, ideally leading to a remission of the subject's cancer.

In certain embodiments, methods are provided for reducing proliferation of a cancer cell comprising priming at least one CD3/CD28-expanded T cell, as described above, against a cancer in the presence of at least one of IL-7, IL-12, and IL-15, or a combination thereof, to generate at least one tumor-specific cytotoxic T cell, and contacting a cancer cell with the at least one cytotoxic T cell. In some embodiments, the cancer cell may be from the same subject to whom the tumor-specific cytotoxic T cell is administered.

"Administering" refers to administration of the compounds as needed to achieve the desired effect. Administration may include, but is not limited to, oral, sublingual, intramuscular, subcutaneous, intravenous, transdermal, topical, parenteral, buccal, rectal, and via injection, inhalation, and implants.

Agents such as IL-7 and anti-CD3/CD28 antibody can be provided (e.g., contacted, reacted, administered, etc.) to one or more T cells by adding them in an appropriate carrier (e.g., buffer) to cell culture medium at concentrations typically ranging from 0.01 ng to about 100 mg/mL, or in some embodiments from about 10 ng to about 50 mg/mL. In some embodiments one or more a commercial reagent(s) can provide the agents, either as solutions, lyophilized powders, or attached to a substrate (e.g., beads such as, for example ClinExVivo Dynabeads (Dynal/Invitrogen Corp.)). Where amounts and/or concentration of a particular reagent is not revealed and/or unavailable, (e.g., the amount of absorbed CD3/CD28 mAbs on a bead) one of skill in the art will be able to determine effective amounts based on proliferation and response of the T cells in response to contacting. In an embodiment, T cells can be co-localized with a cell producing any one of IL-7, anti-CD3/CD28 antibody, IL-12, or IL-15, or any combination thereof (e.g., a cell transfected with a polynucleotide encoding any one or combination of those agents). IL-7, anti-CD3/CD28 antibody, IL-12, and/or IL-15, in any combination that is secreted from such agent-producing cells can induce proliferation of T cells in proximity to the agent-producing cells. Agents may be connected to a tag, including, but not limited to, paramagnetic beads such as ClinExVivo™ Dynabeads® from Dynal/Invitrogen Corp (Sammamish, Wash.). Similarly, anti-CD3/CD28 antibody derived beads are commercially available.

"Co-administered" refers to simultaneous or sequential administration. A compound may be administered before, concurrently with, or after administration of another compound.

The term "contacting a cell" is used to mean contacting a cell in vitro, ex vivo, or in vivo (i.e. within a subject, such as a mammal, including without limitation humans, mice, rats, rabbits, cats, and dogs). Contacting may occur as a result of administration to a subject.

"Reducing proliferation of a cell" refers to reducing, inhibiting, or preventing the growth or differentiation of a cell, including killing a cell.

Cancer may include sarcomas, carcinomas (e.g. small cell lung cancer, and ovarian cancer), lymphomas, or germ cell tumors. A cancer cell may include, but are not limited to, ovarian, lung, head, colorectal, rectal, gastric, heart, liver, pancreatic, bladder, prostate, colon, breast, testicular, brain, skin, esophageal, tracheal, head and neck, lymphoid, leukemia, glioblastoma, vulvar, melanoma, mesothelioma, renal, thyroid, soft tissue, and bone cancer cells. In certain embodiments, the cancer cell may be a lymphoma and/or a leukemia cell.

The use of the terms "a" and an and the and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. All methods described herein can be performed in any suitable order unless otherwise indicated herein or otherwise clearly contradicted by context. The use of any and all examples, or exemplary language (e.g., "such as") provided herein, is intended merely to illustrate aspects and embodiments of the disclosure and does not limit the scope of the claims.

EXAMPLES

Example 1

Materials and Methods

Specimens

Frozen umbilical cord blood samples not eligible for clinical use were obtained from research units at the Duke Stem Cell Laboratory. Eligible patients were consented on an IRB-approved protocol to obtain fibroblasts and ≤3% aliquots of their DCB grafts.

T Cell Enrichment and Expansion System

CD3+ T cells were enriched by negative immunomagnetic selection with EasySep® (StemCell Technology) as described (Mazur M A, Davis C C, Szabolcs P. Ex vivo expansion and Th1/Tc1 maturation of umbilical cord blood T cells by CD3/CD28 costimulation. Biol Blood Marrow Transplant 2008, 14, 1190-6). Expansion was started at 6-8× $10^5$ T cells/mL in gas permeable VueLife®Teflon bags (American Fluoroseal, Gaithesburg, Md.). T cells were co-cultured with ClinExVivo™ Dynabeads® (DynalInvitrogen Corp, WA) at a cell:bead ratio of 3:1 in X Vivo-15 (BioWhittacker, Walkersville, Md.), supplemented with $5.5 \times 10^{-5}$M of BME, 10 mM Hepes, 5% PHS (Valley Biomedical, Winchester, Va.) and 100 p/mL IL-2 (Proleukin, Novartis, Hanover, N.J.), ±10 ng/mL of IL-7 (R&D Systems, Minneapolis, Minn.) as indicated. Medium and cytokines were replenished three times per week to maintain a cell concentration of ~1×$10^6$ TNC/mL. After 12-14 days, after vigorous agitation, the beads were removed by a Dynal magnet: MPC-2 or Dynal ClinExVivo™ MPC™.

Immunophenotypic and Functional Characterization of the CD3/CD28-expanded T Cells Surface and intracellular immunophenotyping, cytokine secretion, T cell enumeration was performed by 4-color FACS as described (Mazur M A, Davis C C, Szabolcs P. Ex vivo expansion and Th1/Tc1 maturation of umbilical cord blood T cells by CD3/CD28 costimulation. Biol Blood Marrow Transplant 2008, 14, 1190-6; Szabolcs P, Park K D, Reese M, Marti L, Broadwater G, Kurtzberg J. Coexistent naive phenotype and higher cycling rate of cord blood T cells as compared to adult peripheral blood. Exp Hematol 2003, 31, 708-14; and Szabolcs P, Park K D, Marti L, et al. Superior depletion of alloreactive T cells from peripheral blood stem cell and umbilical cord blood grafts by the combined use of trimetrexate and interleukin-2 immunotoxin. Biol Blood Marrow Transplant 2004, 10, 772-83). Acquisition of >5,000 CD3+ events was performed on FACSCalibur or FACSCanto II (BD Biosciences, San Jose, Calif.). All antibodies including isotype-specific controls were purchased from BD except anti-Granzyme B was from Serotec (Raleigh, N.C.). Cytotoxicity was measured against IM9 cell line (Harris D T, LoCascio J, Besencon F I. Analysis of the alloreactive capacity of human umbilical cord blood: implications for graft-versus-host disease. Bone Marrow Transplant 1994, 14, 545-53) or recipient fibroblasts by Delfia®EuTDA cytotoxicity assay on a Victor 2 microplate reader (both from PerkinElmer, Boston, Mass.). Following 7-9 days of pre-stimulation with Mitomycin C-treated targets (Sigma, 100 mcg/mL) in the presence of IL-7 (5 ng/mL) and IL-2 (25 U/mL), effectors were washed and cultured in serial dilution with 5000 fresh untreated targets for 2 and 3 h. Percent specific europium chelated ligand (EuTDA) release was calculated: [Experimental release (counts)−Spontaneous release (counts)]/[Maximum release (counts)−Spontaneous release (counts)]×100. Percent spontaneous release=[(Spontaneous release (counts)−background (counts)]/[Maximum release (counts)−background (counts)]×100.

TCRVβ spectratyping and DKL analysis was performed as previously published (Kepler T B, He M, Tomfohr J K, Devlin B H, Sarzotti M, Markert M L. Statistical analysis of antigen receptor spectratype data. Bioinformatics 2005, 21, 3394-400).

Leukemia-specific CTL Generation from CD3/CD28-expanded Cultures

CD3/CD28-expanded 'day 14' T cells generated from CB grafts were cultured in parallel with 2 different Mitomycin C-treated leukemia cells (IM9 and U937) at a stimulator: responder ratio of 1:10 in 24 well plates (Costar, Corning, N.Y.) at ~1×$10^6$ cells/mL. IM9 leukemia cell line represents a lymphoid malignancy (20), while U937 monoblastoid leukemia cells are of myeloid origin (Stonehouse T J, Woodhead V E, Herridge P S, et al. Molecular characterization of U937-dependent T-cell co-stimulation. Immunology 1999, 96, 35-47). CTL were cultured in X Vivo-15 medium (Lonza, Md.) supplemented with 5% fetal calf serum (Gibco, Invitrogen), 5 ng/mL of IL-7, 5 ng/mL IL-15, and 10 ng/mL IL-12 (all from R&D Systems) for 9-10 days. U937 cells were treated in vitro with IFNγ (R&D Systems) at 500 U/mL for ~48 h prior to Mitomycin treatment to enhance their immunogenicity. Cultures were restimulated with Mitomycin C-treated leukemia cells twice. First, in the presence of IL-7 and IL-15, and second with IL-15 alone, each for 6-7 days. CTL cultures were refed with medium alone after half the medium was removed the night before culture termination. Washed effectors were tested in Delfia®EuTDA cytotoxicity assay as described above against fresh, unmanipulated BATDA®-loaded targets that included IM9 and U937 leukemia cells and PHA blasts of the CB transplant recipient. Percent specific EuTDA release was calculated as described above.

Analysis of Human TRC Gene Rearrangement

The signal joint TCR excision circles (sjTREC) assay was performed using real-time quantitative polymerase chain reaction (RT-qPCR) by quantifying the episomal circles generated as a by-product of TCRa gene re-arrangement as previously published (Klein A K, Patel D D, Gooding M E, et al. T-Cell recovery in adults and children following umbilical cord blood transplantation. Biol Blood Marrow Transplant 2001, 7, 454-66). For each cell suspension prepared for TREC analysis total nucleated cell count and absolute T cells content was enumerated by Trucount FACS as previously described (Mazur M A, Davis C C, Szabolcs P. Ex vivo expansion and Th1/Tc1 maturation of umbilical cord blood T cells by CD3/CD28 costimulation. Biol Blood Marrow Transplant 2008, 14, 1190-6; and Szabolcs P, Park K D, Reese M, Marti L, Broadwater G, Kurtzberg J. Coexistent naive phenotype and higher cycling rate of cord blood T cells as compared to adult peripheral blood. Exp Hematol 2003, 31, 708-14) and thereafter dry pellets were prepared and kept frozen at −80° C. until batched matched pairs were thawed. TREC content was expressed after adjustment for $10^5$ T cell/sample.

Statistical Analysis

Two sided paired student t-test was employed to compare conditions±IL-7 and to compare T cell cytotoxicity against the described targets. Statistical significance was set at P values<0.05.

Example 2

Favorable Impact of IL-7 on CB T Cell Survival, Proliferation, and TCR Vβ Repertoire During CD3/CD28 Mediated Expansion Purified T cells obtained from frozen/thawed cord blood specimens were split and cultured in parallel with and without IL-7. Briefly, frozen/thawed cord blood T cells were enriched by negative selection, enumerated by lyse/no wash Multitest T cell® staining in Trucount® tubes (BD) as previously described (Szabolcs P, Park K D, Reese M, Marti L, Broadwater G, Kurtzberg J. Coexistent naive phenotype and higher cycling rate of cord blood T cells as compared to adult peripheral blood. Exp Hematol 2003, 31, 708-14; and Szabolcs P, Park K D, Reese M, Marti L, Broadwater G, Kurtzberg I. Absolute values of dendritic cell subsets in bone marrow, cord blood, and peripheral blood enumerated by a novel method. Stem Cells 2003, 21, 296-303), then split equally into two under identical culture conditions except for the presence of IL-7 as indicated. Cells were cultured for 12-14 days with ClinExVivo™ Dynabeads® while medium and cytokines were replenished 3 times per week. A 50 µL aliquot was removed from the bags at indicated time points, and absolute T cells number was enumerated in Trucount® tubes. Matched pair analysis demonstrated significantly more viable T cells when IL-7 was added to IL-2 in the medium leading to an average of 165 fold T cell expansion (Table 1 and FIG. 1A). For Table 1, surface and intracellular phenotyping, PMA/ionomycin induced cytokine secretion was performed as described (Fujita Y, Rooney C M, Heslop H E. Adoptive cellular immunotherapy for viral diseases. Bone Marrow Transplant 2008, 41, 193-8; Goodwin V J, Sato T A, Mitchell M D, Keelan J A. Anti-inflammatory effects of interleukin-4, interleukin-10, and transforming growth factor-beta on human placental cells in vitro. Am J Reprod Immunol 1998, 40, 319-25; and Marchant A, Goldman M. T cell-mediated immune responses in human newborns: ready to learn? Clin Exp Immunol 2005, 141, 10-8). The signal joint TCR excision circles (sjTREC) were measured before and after expansion, n=4, as published previously (Klein A K, Patel D D, Gooding M E, et al. T-Cell recovery in adults and children following umbilical cord blood transplantation. Biot Blood Marrow Transplant 2001, 7, 454-66). For each sample total nucleated cell count and absolute T cell content were enumerated by Trucount FACS method (Mazur M A, Davis C C, Szabolcs P. Ex vivo expansion and Th1/Tc1 maturation of umbilical cord blood T cells by CD3/CD28 costimulation. Biol Blood Marrow Transplant 2008, 14, 1190-6; and Szabolcs P, Park K D, Reese M, Marti L, Broadwater G, Kurtzberg J. Coexistent naive phenotype and higher cycling rate of cord blood T cells as compared to adult peripheral blood. Exp Hematol 2003, 31, 708-14). TREC content was expressed after adjustment for $10^5$ T cells/sample. Following 14 days of expansion, striking dilution of TCR excision circles was noted as the sjTREC content in CD3+ T cells was depleted by ~2 log in both culture conditions as compared to the starting population of pre-expansion cord blood T cells (FIG. 1B), irrespective of IL-7 exposure. In other words, irrespective of IL-7 in the culture medium, expansion led to dilution and near complete loss of sjTREC in day 14 progeny. There was no significant difference in Trypan Blue viability between the culture conditions, typically >85% by days 12-14. This was in stark contrast once cellular events at the end of 12-14 days of culture were examined by flow cytometry.

TABLE 1

Surface and intracellular (ic) characterization of the expanded progeny (Mean, +/−SD)

| Variable | IL2 Only | IL2 + IL7 | p-value* |
|---|---|---|---|
| Day 12-14 Mean-fold expansion | 48 +/− 21 | 165 +/− 123 | 0.04 |
| % Viable T Lymphocytes among CD45+ events | 46 +/− 15 | 71 +/− 10 | 0.002 |
| % CD4+ | 60 +/− 20 | 65 +/− 16 | 0.26 |
| % CD8+ | 52 +/− 26 | 45 +/− 20 | 0.15 |
| % CD4+/CD8+ | 6 +/− 5 | 3 +/− 3 | 0.43 |
| ic BCL-2/CD3+ (MFI) | 82 +/− 19 | 82 +/− 16 | 0.97 |
| % ic Ki67+/CD3+ "proliferating" | 50 +/− 14 | 65 +/− 11 | 0.003 |

TABLE 1-continued

Surface and intracellular (ic) characterization of the expanded progeny (Mean, +/−SD)

| Variable | IL2 Only | IL2 + IL7 | p-value* |
|---|---|---|---|
| % ic Ki67+/CD4+"proliferating" | 50 +/− 15 | 62 +/− 10 | 0.03 |
| % ic Ki67+/CD8+ "proliferating" | 52 +/− 12 | 68 +/− 11 | 0.001 |
| % ic Activated Caspase 3+/CD3+ "apoptotic" | 8 +/− 3 | 4 +/− 2 | 0.011 |
| % ic Activated Caspase 3+/CD4+ "apoptotic | 7 +/− 3 | 4 +/− 2 | 0.02 |
| % ic Activated Caspase 3+/CD8+ "apoptotic" | 8 +/− 5 | 4 +/− 2 | 0.03 |
| % CD25+/CD3+ | 62 +/− 14 | 63 +/− 17 | 0.95 |
| % CD25+/CD45RO++ | 43 +/− 19 | 25 +/− 28 | 0.08 |
| % CD28+/CD3+ | 89 +/− 5 | 95 +/− 3 | 0.02 |
| % CDRA+/RO−"naïve" | 45 +/− 30 | 78 +/− 28 | 0.06 |
| % CDRA−/RO+ "memory" | 10 +/− 4 | 18 +/− 27 | 0.65 |
| % CDRA+/CD62L+ "phenotypically naïve" | 73 +/− 14 | 90 +/− 5 | 0.03 |
| % CDRA+/CD27+/CD8+ "naïve CD8+" | 79 +/− 7 | 90 +/− 4 | 0.003 |
| % CDRA−/CD27+/CD8+ "central memory" | 13 +/− 6 | 4 +/− 2 | 0.002 |
| % CDRA+/CD27−/CD8+ "effector CTL" | 7 +/− 6 | 6 +/− 4 | 0.26 |
| % CD57+/CD28−/CD8+ "effector CTL" | 0 +/− 0 | 0 +/− 0 | 0.35 |
| % HLA-DR+/CD3+ "activated" | 46 +/− 12 | 44 +/− 11 | 0.53 |
| % HLA-DR+/CD4+ "activated" | 45 +/− 12 | 37 +/− 11 | 0.1 |
| % HLA-DR+/CD8+ "activated" | 45 +/− 16 | 53 +/− 15 | 0.003 |
| % NKG2D+/CD3+ | 38 +/− 23 | 27 +/− 20 | 0.03 |
| % NKG2D+/CD 137 −/CD8+ "resting" | 73 +/− 17 | 62 +/− 26 | 0.05 |
| % NKG2D−/CD137+/CD8+ "activated" | 1 +/− 2 | 0 +/− 0 | 0.32 |
| % NKG2D−/CD137−/CD8+ "anergic" | 24 +/− 16 | 37 +/− 26 | 0.07 |
| % NKG2D+/CD137+/CD8+ "cyotoxic" | 2 +/− 3 | 1 +/− 1 | 0.24 |
| % ic GranzymeA +/CD8+ | 44 +/− 26 | 44 +/− 23 | 0.95 |
| % ic GranzymeB+/CD8+ | 41 +/− 35 | 35 +/− 25 | 0.26 |
| % ic Perforin+/CD8+ | 6 +/− 4 | 4 +/− 2 | 0.10 |
| % ic INFy+/CD3+ | 20 +/− 8 | 19 +/− 10 | 0.64 |
| % ic TNFα +/CD3+ | 50 +/− 20 | 55 +/− 27 | 0.65 |
| % ic IL2+/CD4+ | 79 +/− 9 | 54 +/− 36 | 0.41 |
| % ic IL4+/CD3+ | 2 +/− 2 | 2 +/− 2 | 0.55 |
| % OX40+/CD4+ | 83 +/− 24 | 78 +/− 21 | 0.79 |

*= 2-tailed, paired Student t-test,
MFI: Mean Fluorescence Index

Figure 2:
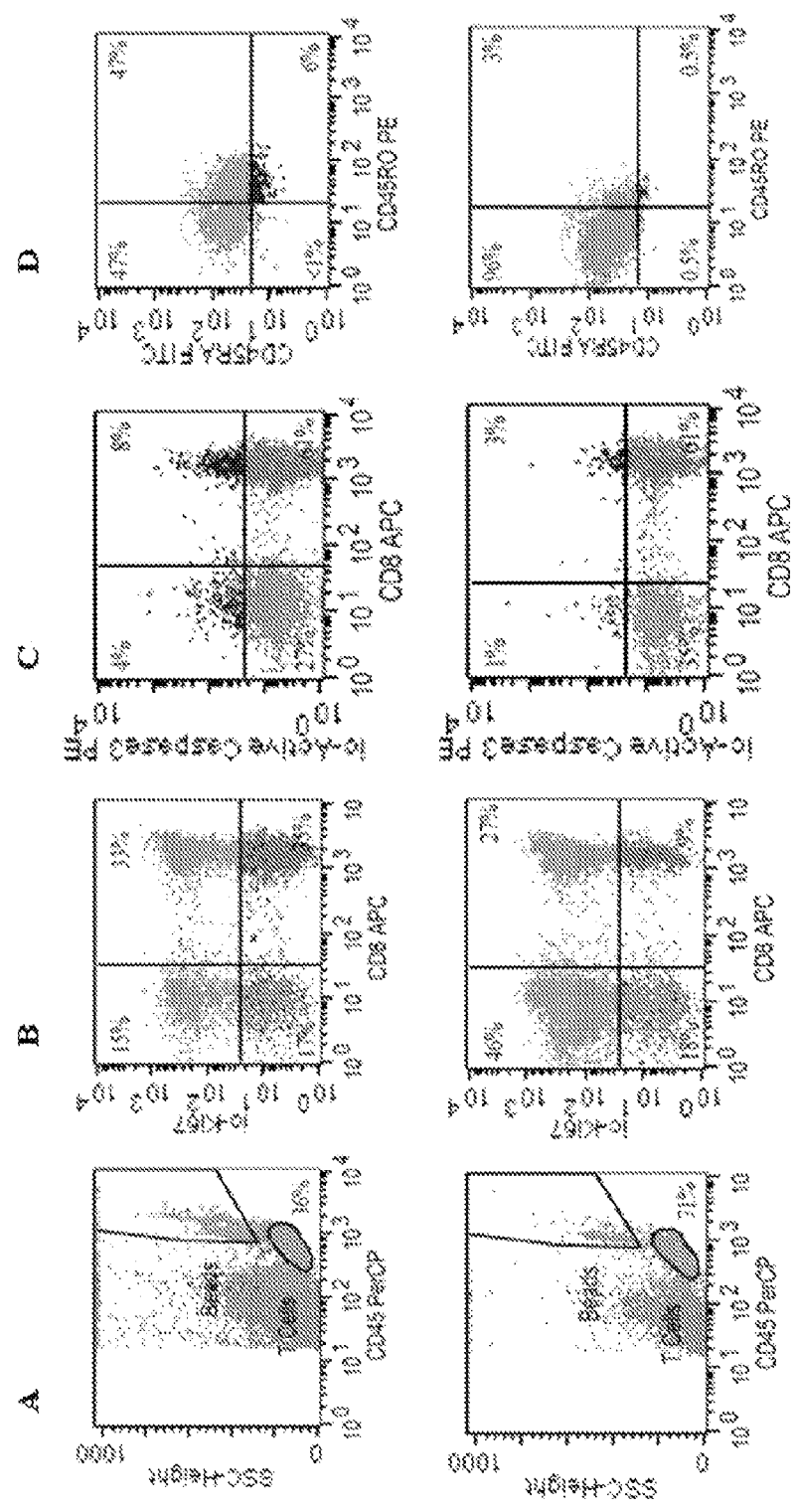
FIG. 2 are flow cytometry profiles for T cells expanded in the presence of IL-2 and IL-7 compared to only IL-2 and stained for (A) CD45-PERCP/SSC, (B) CD8 APC/icKI-67, (C) CD* APC/intracellular (ic)ActiveCasp-3$^+$, and (D) naïve/CD45RA$^+$/RO$^-$.
Figure 3A:
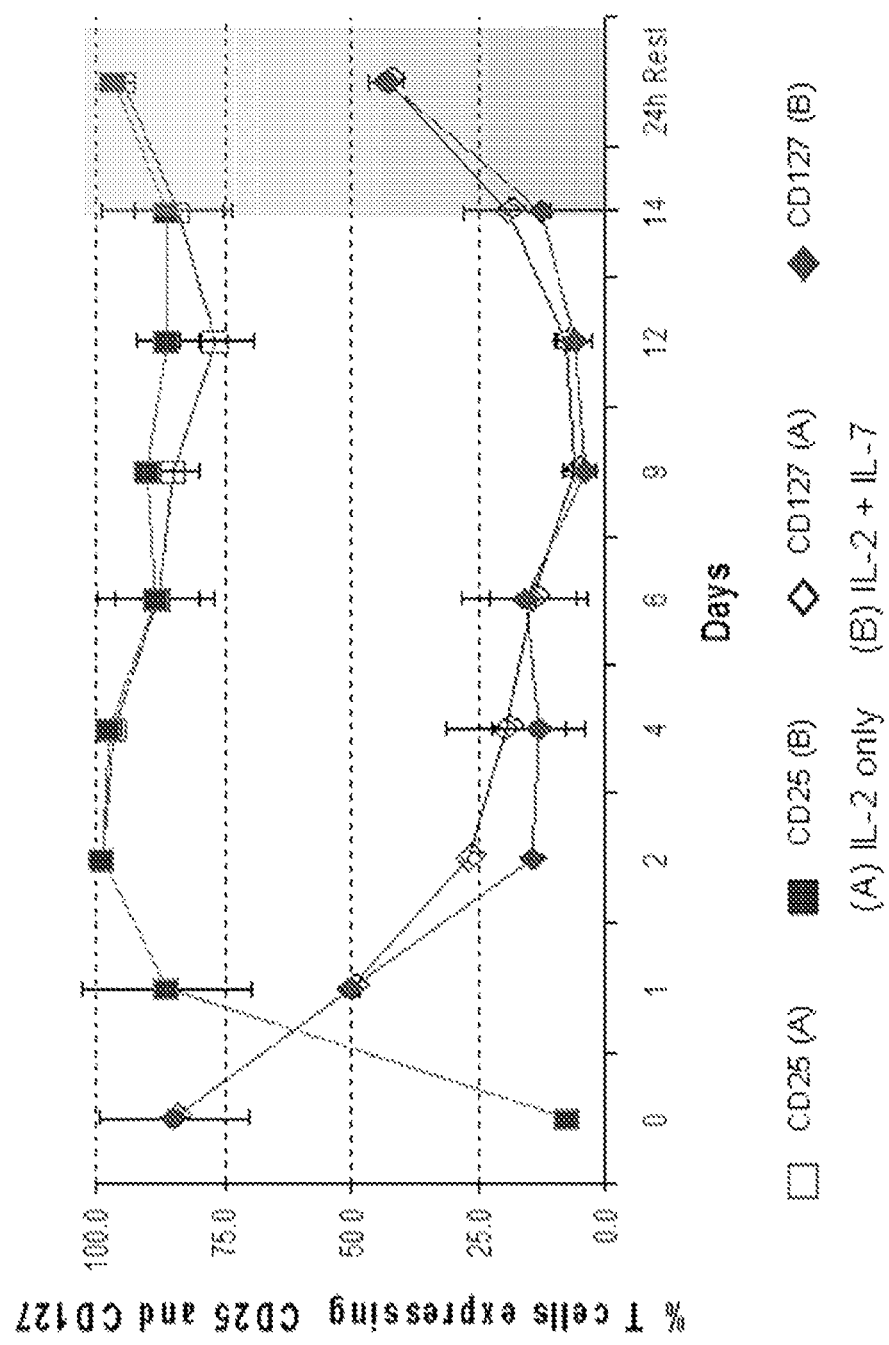
FIG. 3A is a graph of the percentage of T cells expressing CD25 and CD127 over time during expansion.
Figure 3B:
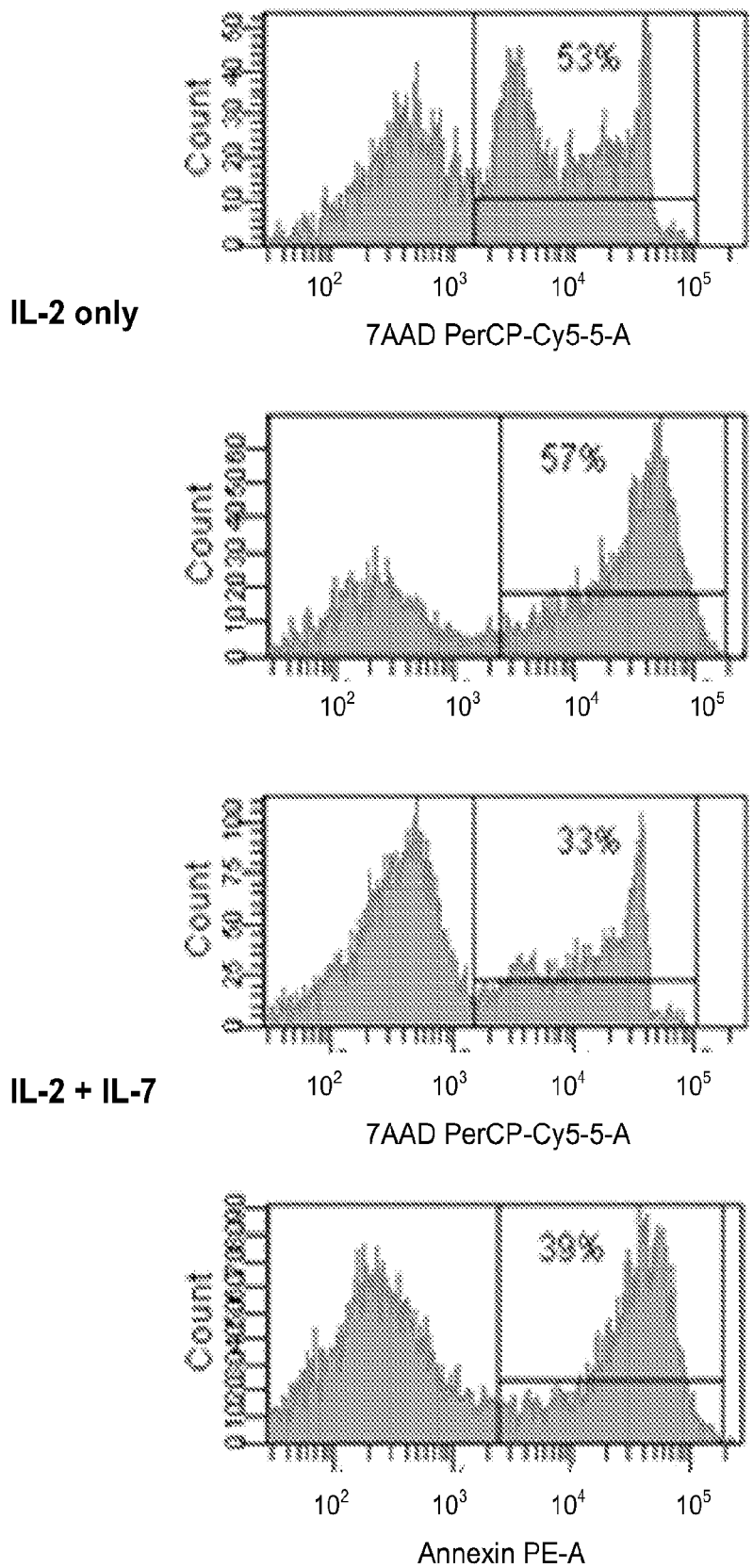
FIG. 3B are graphs of cells stained for Annexin and 7-AAD in parallel after freeze and thaw of expanded day 14 T cells.

Surface and intracellular (ic) FACS characterization was performed as shown previous (Mazur M A, Davis C C, Szabolcs P. Ex vivo expansion and Th1/Tc1 maturation of umbilical cord blood T cells by CD3/CD28 costimulation. Biol Blood Marrow Transplant 2008, 14, 1190-6; Szabolcs P, Park K D, Reese M, Marti L, Broadwater G, Kurtzberg J. Coexistent naive phenotype and higher cycling rate of cord blood T cells as compared to adult peripheral blood. Exp Hematol 2003, 31, 708-14; and Szabolcs P, Park K D, Marti L, et al. Superior depletion of alloreactive T cells from peripheral blood stem cell and umbilical cord blood grafts by the combined use of trimetrexate and interleukin-2 immunotoxin. Biol Blood Marrow Transplant 2004, 10, 772-83). The relative size of T cell subsets in each quadrant was expressed as the percentage of total viable T cells (see Table 1 for p values). Significantly more viable CD45 bright T lymphocytes were identified in cultures supplanted with IL-7 (71%±10)) compared to cultures with IL-2 alone (mean 46%±15) (FIG. 2A, Table 1). As shown in FIG. 2A, CD45-PERCP/SSC defined an unambiguous region of viable cells. All other CD45 dim cells (recently apoptotic) stained also dim for CD3. CD3/CD28-costimulated lymphocytes that have recently undergone apoptosis can be accurately enumerated with the aid of a simple flow cytometry gating strategy. Recently apoptotic/dead cells displayed altered physical properties, as defined by FSC/SSC, additionally stained less intensely with CD45 (and CD3) compared to "viable" lymphocytes (FIG. 3A). As shown in FIG. 2B, icKI-67 staining (upper quads) identified more proliferating T cells when expanded with IL-7 than without. For FIG. 3A, simultaneous monitoring of IL-2Rα (CD25) and IL-7Rα (CD127) was performed after FACS surface staining and acquisition as described on serial aliquots obtained before (day 0) and during expansion on the indicated days. T cells that recently entered the apoptosis pathway were also tracked and identified/gated in the "viable" CD45/FSC/SSC region by intracellular (ic) expression of activated Caspase-3 (FIG. 2C) and 7-AAD/Annexin stain as well (FIG. 3B). As shown in FIG. 2C, when expanded without IL-7, more T cells underwent apoptosis and stained with intracellular (ic) ActiveCasp-3$^+$ even though gated from the viable region of FIG. 2A. For FIG. 3B, cell death after 24 h of rest in cytokine free medium was assayed and scored by positive staining for Annexin and 7-AAD in parallel after freeze and thaw of expanded day 14 T cells, and the data is representative of four experiments.

Figure 4:
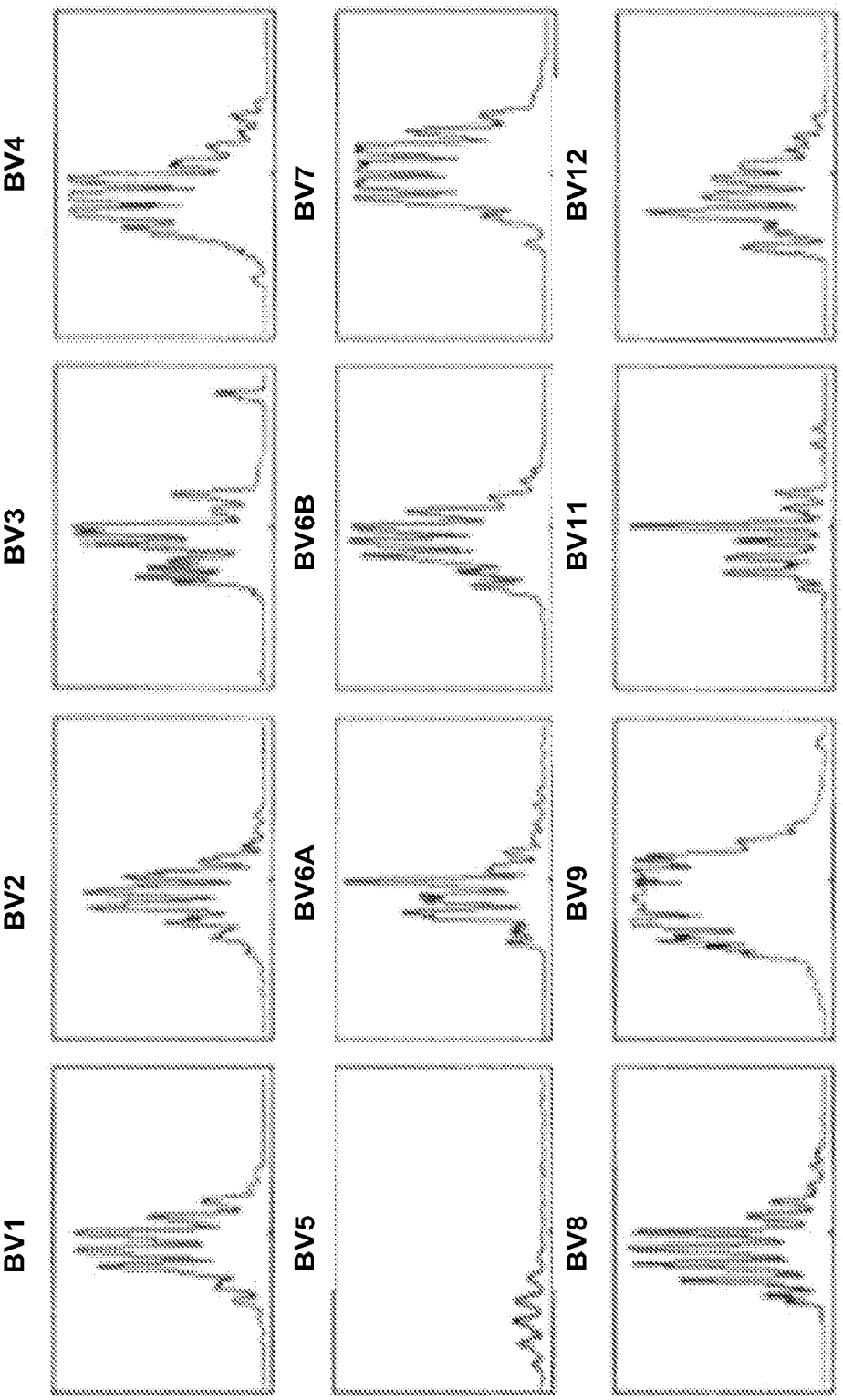
FIG. 4 depicts data from TCRVβ spectratyping of day 14 progeny of an IL-7 supplanted ClinExVivo™ CD3/CD28 co-stimulated culture.

As determined by intracellular (ic) activated Capsase-3 expression, there were significantly fewer T cells undergoing active apoptosis in the presence of IL-7 (median 4% versus 8%) (Table 1, FIG. 3C). The anti-apoptotic effect if IL-7 was evident in both CD4+ and CD8+ subsets (Table 1). To test T cell survival promoting effects of IL-7 beyond the in vitro expansion period, expanded cells were frozen on Day 14 and subsequently thawed and rested for 24 h in culture medium devoid of cytokines. Although the rest period in vitro cannot mimic the in vivo post-infusion conditions exactly, these experiments demonstrate that T cells post expansion retain the potential to up-regulate IL-7 receptor/CD127 (FIG. 3A), and that the majority of IL-7+IL-2 expanded T cells are still alive after freeze, thaw, and 24 hour culture in medium (FIG. 3B). Independent of the described anti-apoptotic effects, IL-7 promoted significantly greater T cell proliferation. About ⅔ of all T cells were still actively cycling at the termination of the expansion period, as detected by intracellular Ki-67 expression (FIG. 2B, Table 1). Since naïve T cells with recent thymic emigrant phenotype (CD28+/CD27+CD45RA+/CD62L+) represent the vast majority of unmanipulated CB T cells, these findings corroborate earlier studies demonstrating the proliferative and anti-apoptotic effects of IL-7 to be operational predominantly in the naive/CD45RA+ T cell compartment. In addition to superior T cell proliferation and reduced apoptosis in IL-7 supplanted conditions, we also found higher TCRVβ diversity per family (p=0.04, n=3) displaying a broad polyclonal spectrum (FIG. 4). FIG. 4 shows day 14 progeny of an IL-7 supplanted ClinExVivo™ CD3/CD28 co-stimulated culture and is representative of three experiments. TCRVβ spectratyping and DKL analysis was performed as previously published (Kepler T B, He M, Tomfohr J K, Devlin B H, Sarzotti M, Markert M L. Statistical analysis of antigen receptor spectratype data. Bioinformatics 2005, 21, 3394-400) and showed that the TCR Vβ repertoire of T cells expanded in the presence of IL-7 displayed high TCR diversity.

Example 3

Limited Th1/Tc1 'Maturation' During Expansion and Low Expression Levels of 4-IBB/CD137, CD40L, and Perforin Correlate with Absent Alloreactivity Once we had demonstrated the salutary effects of IL-7 on T cell viability, expansion, and overall T cell receptor diversity, we determined its impact on surface and intracellular phenotype and overall T cell function as measured by cytokine secretion profile and cytotoxicity. Despite undergoing several cycles of cell division triggered by IL-2+IL-7 in concert with TCR and CD28 co-stimulation, significantly more CB T cells retained the naive starting phenotype, CD45RA+/CD62L+ in the IL-7-containing condition (90%+/−5%) compared to cells cultured in IL-2 alone (73%+/−14%, p=0.03) (FIG. 2D). As shown in FIG. 2D (representative of ten experiments), more T cells displayed the phenotype of naïve/CD45RA⁺/RO⁻ T cells when expanded with IL-7. Surface expression of L-selectin (CD62L) is essential for effective T cell homing to secondary lymphoid organs, a desired destination for antigen inexperienced, unprimed adoptive T cell infusions. CCR-7, a chemokine receptor implicated in both the entry and also in the retaining of T cells in lymph nodes, was also expressed on the majority of expanded T cells, data not shown. Interestingly, while the surface of post-expansion T cells appeared identical to unmanipulated fresh cord blood T cells in terms of CD28+/CD27+/CD45RA+/CD62L co-expression, expanded T cells displayed several upregulated surface molecules commonly seen after activation, including CD25, HLA-DR, OX40, see Table 1. However, <10% of cells expressed CD40L, data not shown. Despite the preservation of resting, naive, 'RTE-mimicking' surface phenotype, as indicated by CD28+/CD27+/CD45RA+/CD62L co-expression, CD3/CD28 co-stimulation led to rapid down-regulation of membrane CD127 (IL 7Ra) in parallel with surface CD25 (IL2Rα) up-regulation on the very same T cells (FIG. 3A). This "receptor switching process" is not dependent on the presence of IL-7 in our cultures as CD25 and CD127 expression levels were superimposable in the presence and absence of IL-7 (FIG. 3A). Moreover, since a near complete reversal between CD25 and CD127 expression has occurred by ~24-48 h of culture (FIG. 3A) this phenomenon appears independent of cell division. Numerical T cell expansion does not begin in earnest in the cultures until Day 3-4, (FIG. 1, and data not shown). Interestingly, when expanded T cells were frozen on Day 14 and subsequently thawed and rested for 24 h in culture medium devoid of cytokines, CD127 was re-expressed on nearly half of the viable T cells (FIG. 3A). IL-7 receptor re-expression could permit delivery of pro-survival signals to expanded T cells administered by clinical DLI infusions in the lymphopenic post-transplant state where endogenous IL-7 level has been demonstrated to be elevated up to 10-30 pg/mL weeks after transplant. Although it is possible that high levels of IL-7 in vivo could induce down-regulation of CD127 in the responding T cells, nevertheless the results suggested that the expanded T cells retained the capacity to re-express CD127 even when rested post-thaw with IL-7 at 15-30 pg/mL.

Figure 5:
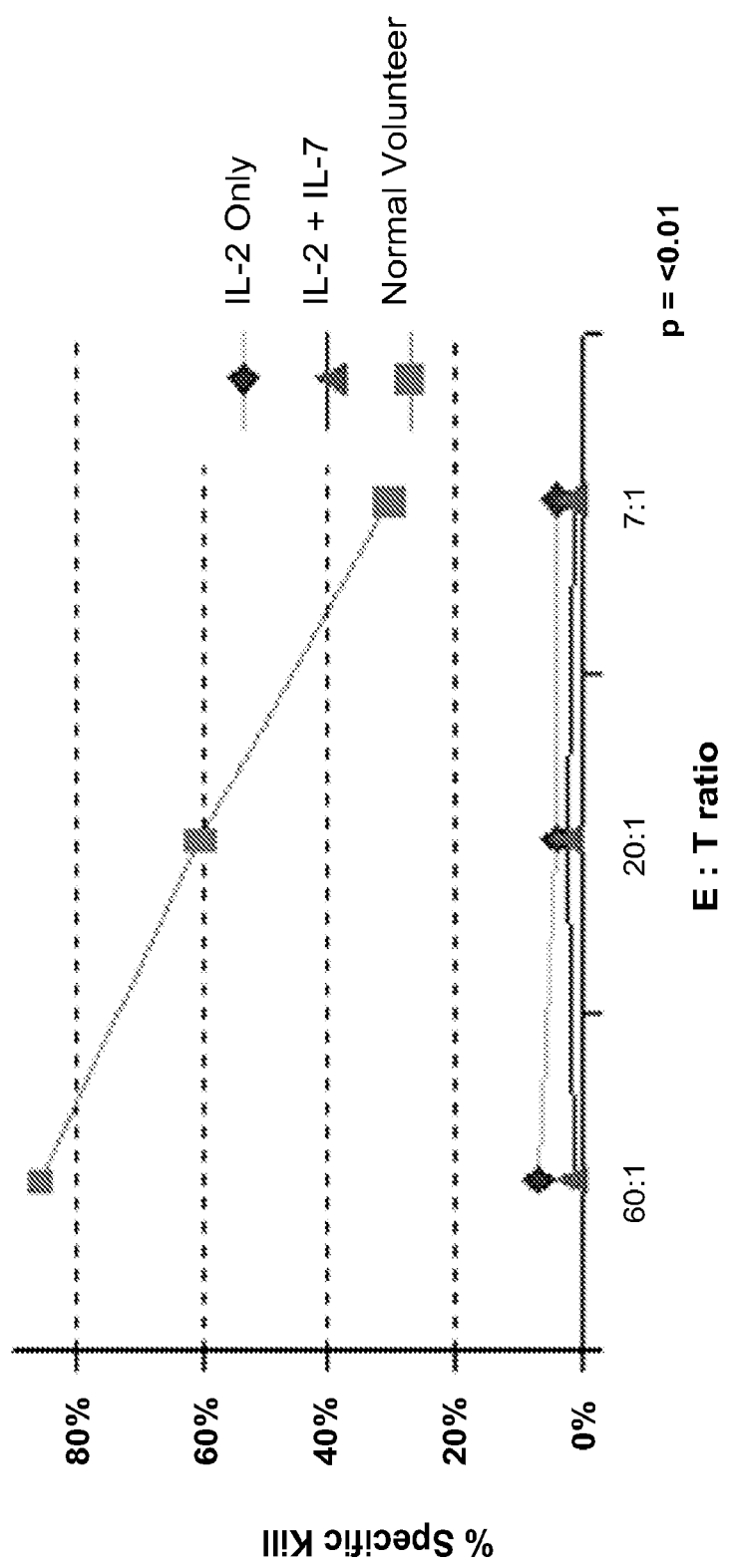
FIG. 5 depicts of europium release (measured by the Delfia EuTDA cytotoxicity assay) as an indicator of specific cytotoxicity for expanded cord blood T cells. The lack of allogeneic cytotoxicity of expanded cord blood T cells is highlighted by use of normal volunteer cells as a positive control, where specific cytotoxicity is presented as a function of the various E:T (effector cell:target cell) ratios.

Effector T cells were obtained from PBL of healthy volunteers as positive controls and compared with CD3/CD28 co-stimulated CB T cells±IL-7. First, effectors were primed/sensitized against a highly immunogeneic (HLA-DR+, CD40+, CD80+, CD86+) IM9 cell line for 7-9 days at 1:1 to 1:3 responder:stimulator ratio, then re-exposed to fresh BATDA®-loaded IM9 targets at E:T ratios for 2 and 3 h. Europium release was measured by the Delfia® EuTDA cytotoxicity assay (Mazur MA, Davis CC, Szabolcs P. Ex vivo expansion and Th1/Tc1 maturation of umbilical cord blood T cells by CD3/CD28 costimulation. Biol Blood Marrow Transplant 2008, 14, 1190-6) and the calculated percent specific cytotoxicity is presented on the Y-axis of FIG. 5. The data is FIG. 5 is representative of seven experiments. CD3/CD28 co-stimulation with ClinExVivo™ Dynabeads® in this series of experiments enhanced in a larger fraction of post-expansion T cells the capacity for intracellular expression of IPNy, TNFα, and Granzyme B (Table 1) than we previously reported using different artificial-APC beads. Nevertheless, despite the potential for an increase in alloreactivity after the more robust expansion in the presence of IL-7, the expanded progeny lacked cytotoxicity against a highly immunogenic (CD40+, CD80+, CD86+) EBV+ allogeneic lymphoblastoid cell line (IM9) (n=7), or recipient fibroblasts (n=2), despite a week long pre-sensitization prior to performing the CTL assay (FIG. 5). Interestingly, absent cytotoxicity coincided with low expression of 4-1BB/CD137, CD40L, and perforin (Table 1). Together, these features supported a favorable safety profile of "Day 14" ClinExVivo™ expanded T cells with reduced likelihood for inducing GVHD in vivo upon adoptive transfer.

Example 4

Cytokines Can Prime ex vivo Expanded, CD3/CD28-costimulated Cord Blood T Cells Against Lymphoid and Myeloid Leukemia Donor leukocyte infusion with "Day 14" ClinExVivo™+IL-2+IL-7 expanded T cells generated from the originally infused cord blood graft could alleviate post-transplant lymphopenia and qualitative T cell defects until thymic regeneration could contribute new T cells. However, such DLI would be antigen non-specific and will require microbial and/or tumor antigens to in vivo prime infused T cells in the transplant recipients. In a series of experiments we evaluated the potential of "Day 14" CD3/CD28-costimulated/expanded T cells to undergo in vitro priming against specific leukemic targets. The data below implies that in vitro generated tumor-specific CTL responses could be adoptively infused to treat leukemia patients with minimal residual disease and/or relapse.

Figure 6:
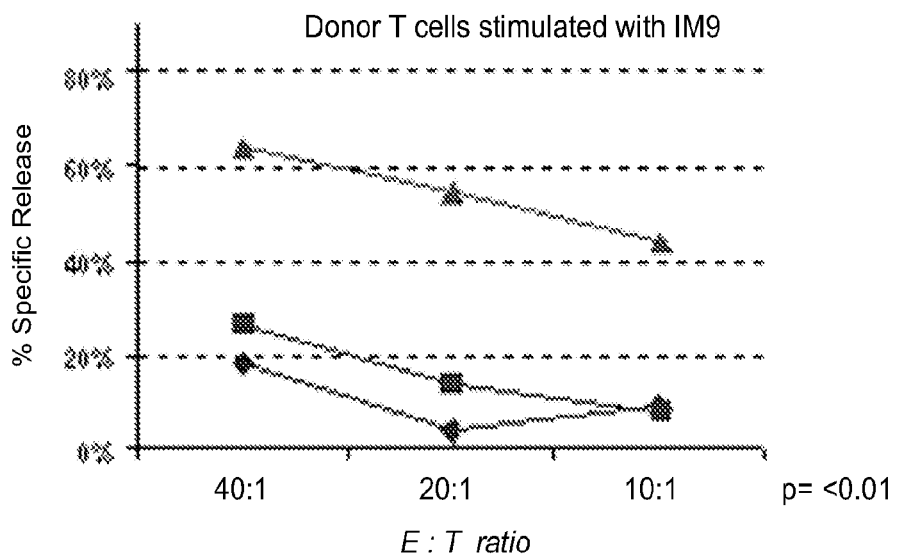
FIG. 6 depicts europium release (measured by the Delfia EuTDA cytotoxicity assay) as an indicator of specific cytotoxicity for (A) CTL primed in vitro with Mitomycin C-treated IM9 cells and (B) CTL primed in vitro with IFNy-treated and Mitomycin C-treated U937 cells. Cultures for both (A) and (B) were expanded in the presence of IL-12, IL-7, and IL-15. Specific cytotoxicity is presented as a function of the various E:T (effector cell:target cell) ratios.
Figure 6:
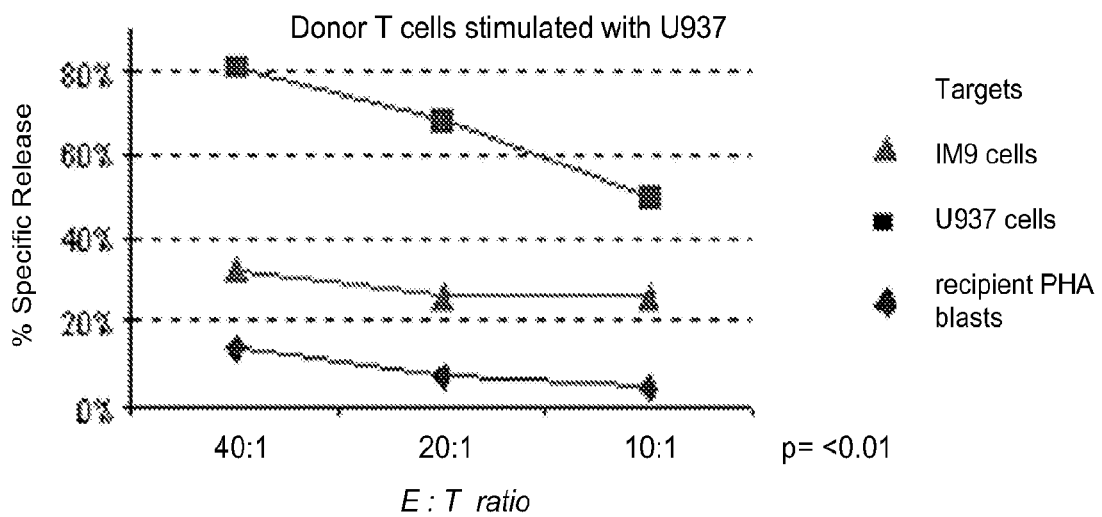

CD3/CD28-expanded "Day 14" T cells were stimulated in vitro for 3 weeks in parallel cultures with killed, Mitomycin C treated lymphoid leukemia cells (IM9) and IFNγ-treated myeloid leukemia cells (U937). U937 cells by themselves cannot induce allogeneic T cell response unless a stimulating anti-CD3 antibody is added to cultures (see, e.g., Stonehouse T J, Woodhead V E, Herridge P S, et al. Molecular characterization of U937-dependent T-cell co-stimulation. Immunology 1999, 96, 35-47). In addition, they do not provide co-stimulation via the CD80/CD86-CD28 pathway, but likely via the ubiquitously expressed CD147, CD98 molecules. CTL priming was performed in the decreasing presence of IL-12, IL-7, and IL-15 drawing from the experimental strategy to in vitro prime anti-viral responses from cord blood (see, e.g., Park K D, et al., *Blood,* (2006);108:1770-3). Briefly, T cells were first CD3/CD28-expanded in the presence of IL-2 and IL-7 over 14 days and thereafter were primed/sensitized against 2 killed leukemia cell lines in parallel cultures (24-well plates (Costar)) at about $1\times10^6$ cells/mL) for 7-9 days at 10:1 responder:stimulator ratio in the presence of IL-12, IL-7, and IL-15 (5 ng/mL of IL-7, 5 ng/mL IL-15, and 10 ng/mL IL-12 (all from R&D Systems)). Each CTL culture was re-stimulated 2 more times (first with IL-7 and IL-15, second with IL-15 alone) for a total of 3 weeks with the respective killed leukemia cells. Cytotoxicity of washed effectors after 3 weeks in CTL culture was tested against fresh, unmodified, BATDA®-loaded IM9, U937 cells, and recipient PHA blasts at the indicated E:T ratios for 3 h, as indicated. Europium release was measured by the Delfia® EuTDA cytotoxicity assay and the calculated percent specific cytotoxicity is presented on the Y-axis of FIG. 5. Robust T cell expansion (195x, ±115, n=4) ensued over the course of ~3 weeks when killed leukemia cells rather than ClinEx Vivo™ beads served APC. After the course of two to three repeated stimulations, strong leukemia-specific cytotoxicity was detected in CTL assays, killing the stimulating leukemia cells but not the other leukemia or most importantly cord blood transplant recipient PHA blasts, n=4, p=<0.01, (FIG. 6A and FIG. 6B). Failure to recognize and kill CB transplant recipient PHA blasts indicated future clinical safety from the potential toxicity of GVHD. FIG. 6A shows CTL primed in vitro with Mitomycin C-treated IM9 cells, and FIG. 6B shows CTL primed in vitro with IFNγ-treated and Mitomycin C-treated U937 cells. The data shown is representative of four experiments.

Example 5

Figure 7:
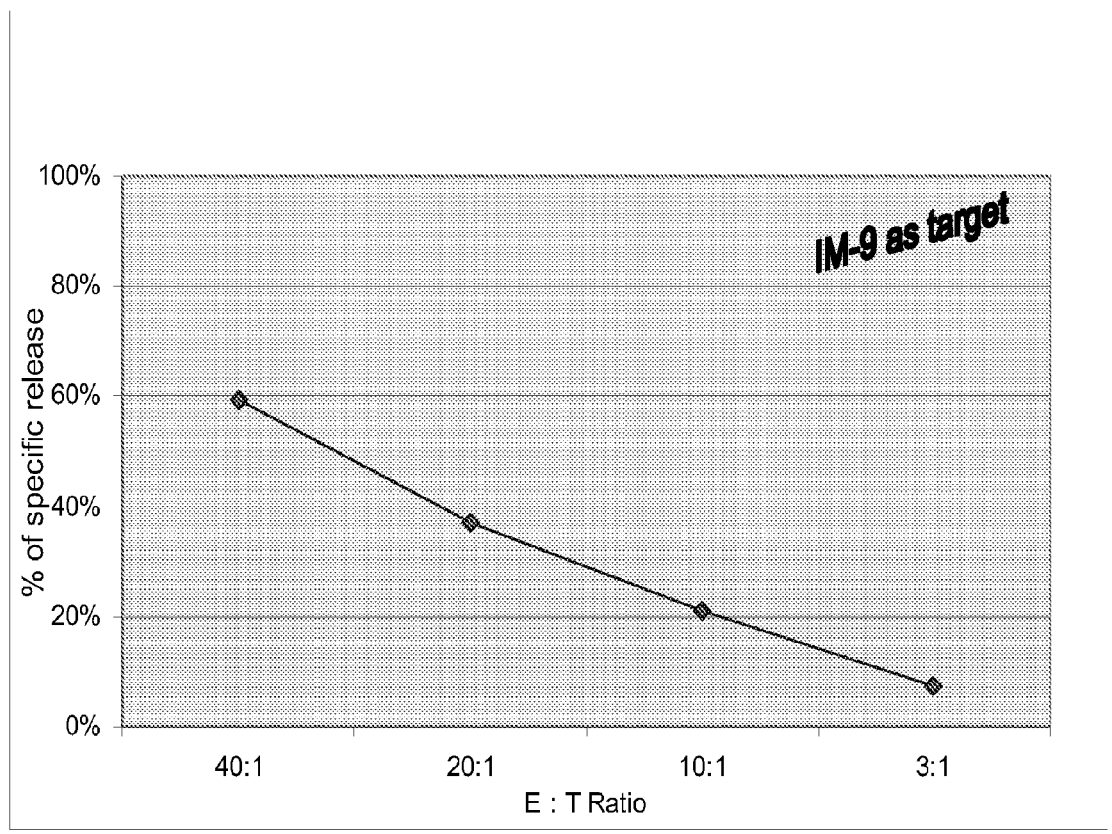
FIG. 7 depicts europium release (measured by the Delfia EuTDA cytotoxicity assay) as an indicator of IM9 specific cytotoxicity of T cells expanded in the presence of IL-12, IL-7, and IL-15, as a function of the various E:T (effector cell:target cell) ratios.
Figure 8:
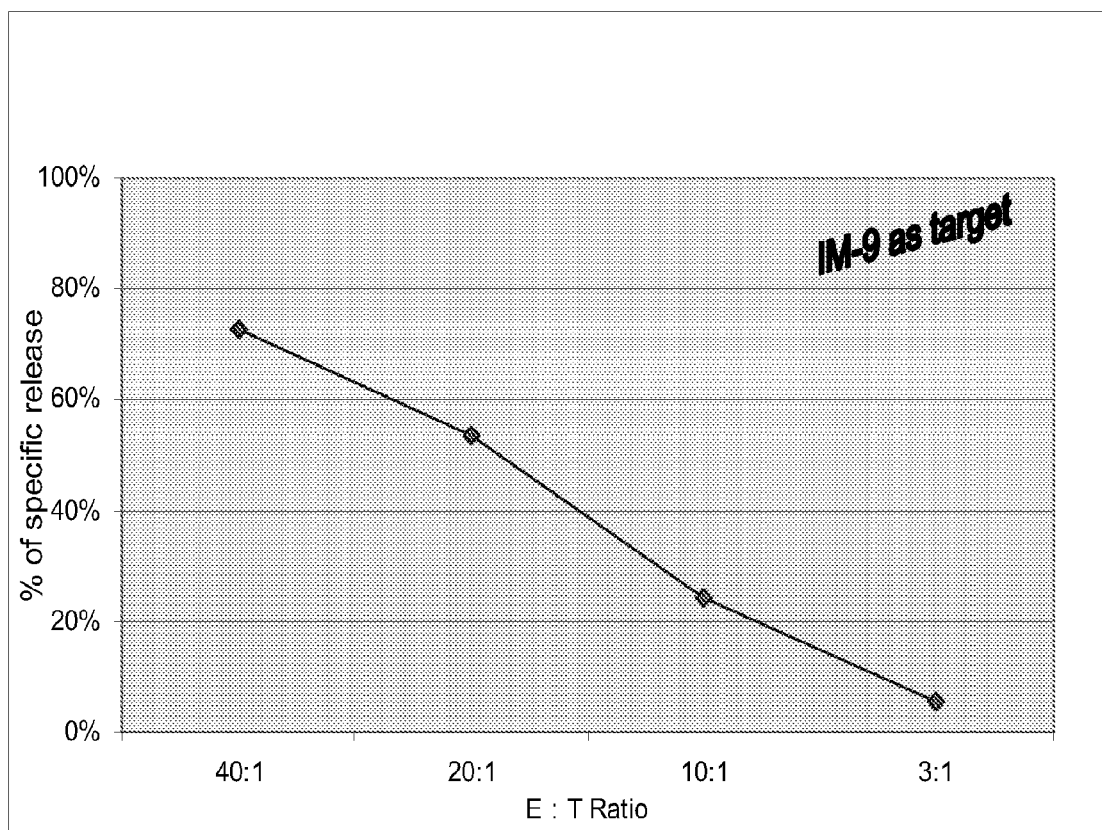
FIG. 8 depicts europium release (measured by the Delfia EuTDA cytotoxicity assay) as an indicator of IM9 specific cytotoxicity of T cells expanded in the presence of IL-15 only, as a function of the various E:T (effector cell:target cell) ratios.

IL-15 is Sufficient for Priming CD3/CD28-costimulated Cord Blood T Cells Against Lymphoid and Myeloid Leukemia Similar to the procedure describe in Example 4, CD3/CD28-expanded "Day 14" T cells (thawed from frozen stock) were split into parallel cultures and stimulated in vitro for 3 weeks with killed, Mitomycin C-treated lymphoid leukemia cells (IM9). CTL priming was performed in the decreasing presence of A.; IL-12, IL7, and IL-15 (5 ng/mL of IL-7, 5 ng/mL IL-15, and 10 ng/mL IL-12 (all from R&D Systems)) (FIG. 7); or IL-15 (5 ng/mL) alone (FIG. 8). Robust T cell expansion was observed in both cultures when killed leukemia cells were provided as APC. After the course of two to three repeated stimulations, strong leukemia-specific cytotoxicity was detected in CTL assays in both conditions (FIGS. 7 and 8). These data demonstrate that IL-15 alone provides sufficient exogenous cytokine support for anti-leukemia activity in these conditions.

What is claimed is:

1. A method of enhancing ex vivo proliferation and activation, relative to no stimulation, of a T cell population from cord blood, the method consisting of contacting the T cell population with IL-7, or a functional fragment thereof, IL-2, or a functional fragment thereof, an anti-CD3 antibody, or a functional fragment thereof, and an anti-CD28 antibody, or a functional fragments thereof, to activate and proliferate the T cell population.

2. The method of claim 1, wherein the anti-CD3 antibody, or functional fragment thereof, or the anti-CD28 antibody, or functional fragment thereof, is linked to a surface.

3. The method of claim 1, wherein the anti-CD3 antibody, or functional fragment thereof, and the anti-CD28 antibody, or functional fragment thereof, are linked to a surface.

4. The method of claim 3, wherein the anti-CD3 antibody, or functional fragment thereof, and the anti-CD28 antibody, or functional fragment thereof, are linked to the same surface.

5. The method of claim 2, wherein the surface comprises a cell culture vessel, a glass particle, a latex particle, a paramagnetic particle, a microparticle, or a nanoparticle.

6. The method of claim 1, wherein the T cell population is induced to proliferate to about 100-fold the original T cell population.

7. The method of claim 1 wherein the expanded T cell population retains the capacity for in vivo proliferation upon transplantation.

* * * * *